United States Patent [19]
Mezes et al.

[11] Patent Number: 5,892,020
[45] Date of Patent: Apr. 6, 1999

[54] MULTIVALENT SINGLE CHAIN ANTIBODIES

[75] Inventors: Peter S. Mezes, Oldlyme, Conn.; Brian B. Gourlie, Concord, Mass.

[73] Assignee: The Dow Chemical Company, Midland, Mich.

[21] Appl. No.: 481,006

[22] Filed: Jun. 7, 1995

Related U.S. Application Data

[60] Division of Ser. No. 263,911, Jun. 21, 1994, which is a continuation-in-part of Ser. No. 990,263, Dec. 11, 1992, abandoned.

[51] Int. Cl.⁶ .................................................. C07H 21/04
[52] U.S. Cl. .................................... 536/23.53; 530/387.3; 135/320.1
[58] Field of Search .................... 536/23.53; 530/387.3; 435/320.1

[56] References Cited

U.S. PATENT DOCUMENTS

| | | | |
|---|---|---|---|
| 4,474,893 | 10/1984 | Reading et al. | 436/547 |
| 4,642,334 | 2/1987 | Moore et al. | 530/388 |
| 4,714,681 | 12/1987 | Reading | 435/240.27 |
| 4,946,778 | 8/1990 | Ladner et al. | 435/69.6 |
| 5,091,513 | 2/1992 | Huston et al. | 530/387 |
| 5,130,297 | 7/1992 | Sharma et al. | 514/8 |
| 5,132,405 | 7/1992 | Huston et al. | 530/387.3 |

FOREIGN PATENT DOCUMENTS

| | | |
|---|---|---|
| 0506124 | 3/1992 | European Pat. Off. . |
| 8809344 | 12/1988 | WIPO . |
| 9119739 | 12/1991 | WIPO . |
| 9311161 | 6/1993 | WIPO . |

OTHER PUBLICATIONS

Huston et al., Methods in Enzymology, 203:46, 1991.
George et al., J. Cell. Biochem., Supplement 15E, p. 127, 1991.
Milenic et al., Cancer Research, 1991, 51:6363.
Huston et al., "Protein Engineering of Antibody Binding Sites: Recovery of Specific Activity in an Anti–digoxin Single–Chain Fv Analogue Produced in *Escherichia coli*", *Proc. Natl. Acad. Sci., Biochemistry*, vol. 85, pp. 5879–5883, Aug. 1988.
Larson, "Improved Tumor Targeting With Radiolabeled Recombinant, Single–Chain, Antigen–Binding Protein", *Journal of the National Cancer Institute*, vol. 82, No. 14, pp. 1173–1174, Jul. 18. 1990.
Colcher et al., In Vivo Tumor Targeting of a Recombinant Single–Chain Antigen–Binding Protein, *Journal of the National Cancer Institute*, vol. 82, No. 14, pp. 1191–1197, Jul. 18. 1990.
Bedzyk et al., "Immunological and Structural Characterization of a High Affinity Anti–fluorescein Single–chain Antibody", *The Journal of Biological Chemistry*, V. 265, No. 30, pp. 18615–18620, Oct. 25, 1990.
Winter et al., "Man–made Antibodies", *Nature*, vol. 349, pp. 293–299, Jan. 24, 1991.

Davis, "Single Chain Antibody (SCA) Encoding Genes: One–Step Construction and Expression in Eukaryotic Cells", *Biotechnology*, vol. 9, pp. 165–169, Feb. 1991.
Whitlow et al., "Single–Chain Fv Proteins and Their Fusion Proteins", *Methods: A Companion to Methods in Enzymology*, vol. 2, No. 2, pp. 97–105, Apr. 1991.
Skerra et al., "The Functional Expression of Antibody $F_v$ Fragments in *Escherichia coli*: Improved Vectors and a Generally Applicable Purification Technique", *Biotechnology*, vol. 9, pp. 273–278, Mar. 1991.
Gibbs et al., "Construction and Characterization of a Single–Chain Catalytic Antibody", *Proc. Natl. Acad. Sci., U.S.A.*, vol. 88, pp. 4001–4004, May 1991.
Hodgson, "Making Monoclonals in Microbes", *Biotechnology*, vol. 9, pp. 421–425, May 1991.
Pluckthun, "Antibody Engineering: Advances From the Use of *Escherichia coli* Expression Systems", *Biotechnology*, vol. 9, pp. 545–550, Jun. 1991.
Bird et al., "Single Chain Antibody Variable Regions", *Trends in Biotechnology*, vol. 9, pp. 132–137 (1991).
Glockshuber et al., "A Comparison of Strategies to Stabilize Immunoglobulin $F_v$–Fragments", *Biochemistry*, vol. 29, pp. 1362–1367 (1990).
Denzin et al., "Single–chain Site–specific Mutations of Fluorescein–Amino Acid Contact Residues in High Affinity Monoclonal Antibody 4–4–20", *Journal of Biological Chemistry*, vol. 266, No. 21, pp. 14095–14103 (1991).
Pantoliano et al., "Conformational Stability, Folding, and Ligand–Binding Affinity of Single–Chain Fv Immunoglobulin Fragments Expressed in *Escherichia coli*", *Biochemistry*, vol. 30, pp. 10117–10125 (1991).
Gregoire et al., "Engineered Secreted T–Cell Receptor $\alpha\beta$ Heterodimers", *Proc. Natl. Acad., Sci., U.S.A.*, vol. 88, pp. 8077–8081, Sep. 1991.
Pack et al., "Miniantibodies: Use of Amphipathic Helices to Produce Functional, Flexibly Linked Dimeric $F_v$ Fragments with High Avidity in *Escherichia coli*", *Biochemistry*, vol. 31, No. 6, pp. 1579–1584 (1992).
Soo Hoo et al., "Characterization of a Single–chain T–cell Receptor Expressed in *Escherichia coli*", *Proc. Natl. Acad. Sci., U.S.A.*, vol. 89, pp. 4759–4763, May 1992.
Novotny et al., "A Soluble, Single–chain T–cell Receptor Fragment Endowed With Antigen–combining Properties", *Proc. Natl. Acad. Sci., U.S.A.*, vol. 88, pp. 8646–8650, Oct. 1991.
Williams et al., "The Immunoglobulin Superfamily–Domains for Cell Surface Recognition", *Ann. Rev. Immunol.*, vol. 6, pp. 381–405 (1988).

(List continued on next page.)

*Primary Examiner*—Frank C. Eisenschenk
*Attorney, Agent, or Firm*—Karen L. Kimble; Mark Scott; Thomas Zindrick

[57] ABSTRACT

The present invention discloses multivalent single chain antibodies which have two or more biologically active antigen binding sites. The multivalent single chain antibodies are formed by using a peptide linker to covalently link two or more single chain antibodies, each single chain antibody having a variable light domain linked to a variable heavy chain domain by a peptide linker.

23 Claims, 20 Drawing Sheets

OTHER PUBLICATIONS

Williams et al., "Structural Diversity in Domains of the Immunoglobulin Superfamily", Cold *Spring Harbor Symposia on Quantitative Biology,* LIV, pp. 637–647, 1989, Cold Spring Harbor Lab. Press.

Hunkapiller et al., "Implications of the Diversity of the Immunoglobulin Gene Superfamily", *Cold Spring Harbor Symposia on Quantitative Biology,* LIV, 1989, pp. 15–29, Cold Spring Harbor Laboratory Press.

Wraith et al., "T–cell Recognition as the Target for Immune Intervention in Autoimmune Disease", *Cell,* vol. 57, pp. 709–715, Jun. 2, 1989.

Adorini, et al., "New Perspective on Immunointervention in Autoimmune Diseases", *Immunology Today,* vol. 11, No. 11, pp. 383–386 (1990).

Bird et al., "Single–Chain Antigen–Binding Proteins", *Science,* vol. 242, pp. 423–426, Oct. 21, 1988.

Skerra et. al., "Assembly of a Functional Immunoglobulin $F_v$ Fragment in *Escherichia coli*", *Science,* vol. 240, pp. 1038–1041, May 20, 1988.

Takkinen et al., "An Active Single–Chain Antibody Containing a Cellulase Linker Domain is Secreted by *Escherichia coli*", *Protein Engineering,* vol. 4, No. 7, pp. 837–841 (1991).

Traunecker et al., "Bispecific Single Chain Molecules (Janusins) Target Cytotoxic Lymphocytes on HIV Infected Cells", *The EMBO Journal,* vol. 10, No. 12, pp. 3655–3659 (1991).

Yokota et al., "Rapid Tumor Penetration of a Single–Chain Fv and Comparison with Other Immunoglobulin Forms", Cancer Research, vol. 52, 3402–3408, Jun. 15, pp. 3402–3408 (1992).

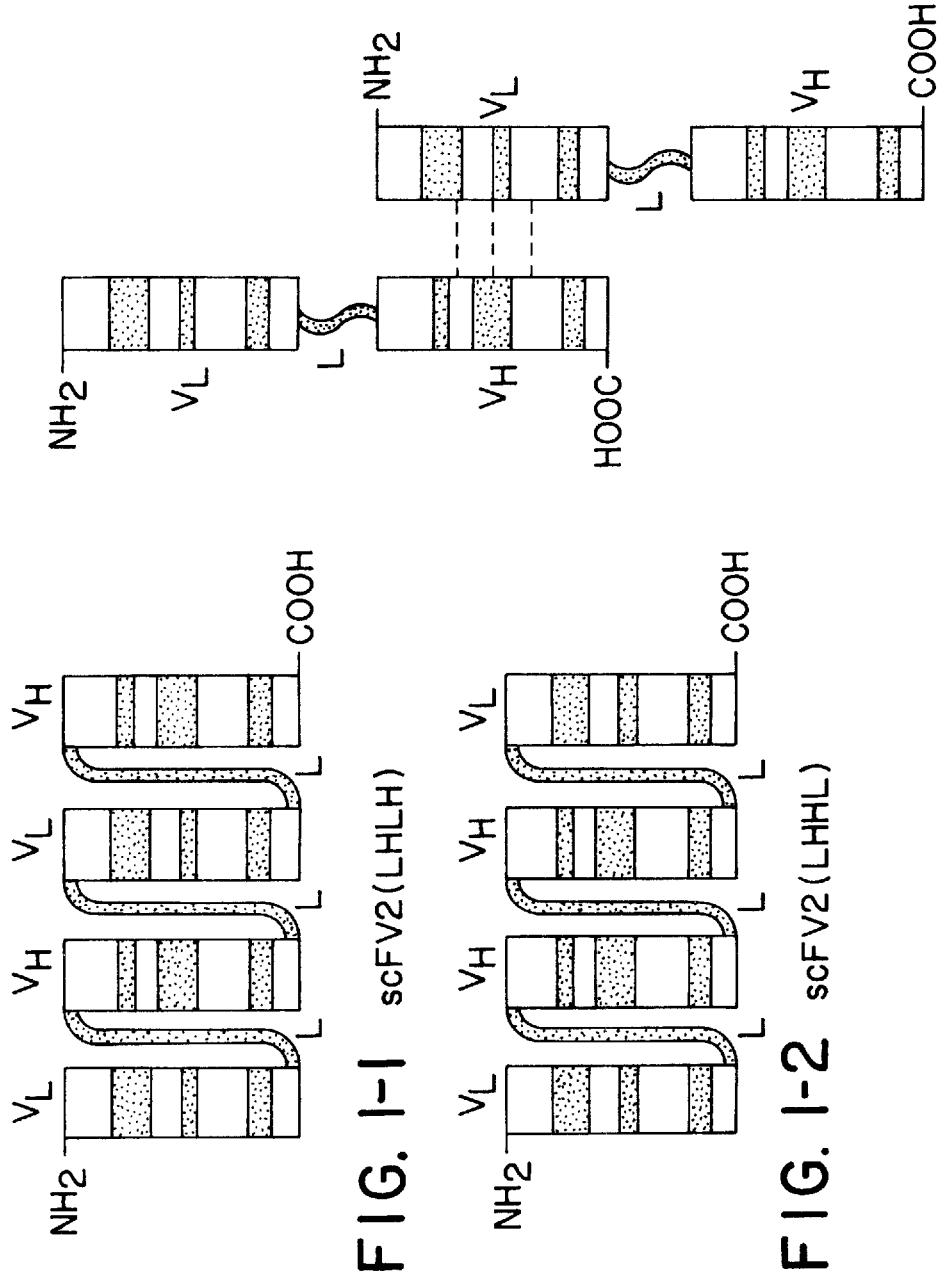

FIG. 2

```
GAC ATT GTG ATG TCA CAG TCT CCA TCC CTA CCT GTG TCA
GTT GGC GAG AAG GTT ACT TTG AGC TGC AAG TCC AGT CAG AGC
CTT TTA TAT AGT GGT AAT CAA AAG AAC TAC TTG GCC TGG TAC
CAG CAG AAA CCA GGG CAG TCT CCT AAA CTG CTG ATT TAC TGG
GCA TCC GCT AGG GAA TCT GGG GTC CCT GAT CGC TTC ACA GGC
AGT GGA TCT GGG ACA GAT TTC ACT CTC ACC ATC AGC AGT GTG
AAG ACT GAA GAC CTG GCA GTT TAT TAC TGT CAG CAG TAT TAT
AGC TAT CCC CTC ACG TTC GGT GCT GGG ACC AAG CTG GTG CTG
AAG
```

FIG. 3

```
Asp Ile Val Met Ser Gln Ser Pro Ser Ser Leu Pro Val Ser Val
Gly Glu Lys Val Thr Leu Ser Cys Lys Ser Ser Gln Ser Leu Leu
Tyr Ser Gly Asn Gln Lys Asn Tyr Leu Ala Trp Tyr Gln Gln Lys
Pro Gly Gln Ser Pro Lys Leu Leu Ile Tyr Trp Ala Ser Ala Arg
Glu Ser Gly Val Pro Asp Arg Phe Thr Gly Ser Gly Ser Gly Thr
Asp Phe Thr Leu Ser Ile Ser Ser Val Lys Thr Glu Asp Leu Ala
Val Tyr Tyr Cys Gln Gln Tyr Tyr Ser Tyr Pro Leu Thr Phe Gly
Ala Gly Thr Lys Leu Val Leu Lys
```

FIG. 4

GAG GTT CAG TTG CAG CAG TCT GAC GCT GAG TTG GTG AAA CCT
GGG GCT TCA GTG AAG ATT TCC TGC AAG GCT TCT GGC TAC ACC
TTC ACT GAC CAT GCA ATT CAC TGG GTG AAA CAG AAC CCT GAA
CAG GGC CTG GAA TGG ATT GGA TAT TTT TCT CCC GGA AAT GAT
GAT TTT AAA TAC AAT GAG AAG TTC AAG GGC AAG GCC ACA CTG
ACT GCA GAC AAA TCC TCC AGC ACT GCC TAC GTG CAG CTC AAC
AGC CTG ACA TCT GAG GAT TCT GCA GTG TAT TTC TGT ACA AGA
TCC CTG AAT ATG GCC TAC TGG GGT CAA GGA ACC TCA GTC ACC
GTC TCC TCA

FIG. 5

Glu Val Gln Leu Gln Gln Ser Asp Ala Glu Leu Val Lys Pro Gly
Ala Ser Val Lys Ile Ser Cys Lys Ala Ser Gly Tyr Thr Phe Thr
Asp His Ala Ile His Trp Val Lys Gln Asn Pro Glu Gln Gly Leu
Glu Trp Ile Gly Tyr Phe Ser Pro Gly Asn Asp Asp Phe Lys Tyr
Asn Glu Arg Phe Lys Gly Lys Ala Thr Leu Thr Ala Asp Lys Ser
Ser Ser Thr Ala Tyr Val Gln Leu Asn Ser Leu Thr Ser Glu Asp
Ser Ala Val Tyr Phe Cys Thr Arg Ser Leu Asn Met Ala Tyr Trp
Gly Gln Gly Thr Ser Val Thr Val Ser Ser

FIG.6A

DNA AND AMINO ACID SEQUENCE OF CC49 V$_L$-L-V$_H$-L-V$_L$-L-V$_H$

```
                      Cla I       EcoR I
5'-C TCA TGT TTG ACA GCT TAT CAT CGA TGA ATT CCA TCA CTT CCC TCC      46
GTT CAT TTG TCC CCG GTG GAA ACG AGG TCA TCA TTT CCT TCC GAA AAA       94
ACG GTT GCA TTT AAA TCT TAC ATA TAT AAT ACT TTC AAA GAC TAC ATT      142
TGT AAG ATT TGA TGT CGG CTG AGT CGT AAA GAT CGT ACG CAA TTA          190
            PENPR1- AAC ACT GTA GGG ATA GTG GAA                      238
TTG TTT CGT GAT TGT TCA AGC CAT AAC ACT GTA GGG ATA GTG GAA AGA
GTG CTT CAT CTG GTT ACG ATC AAT CAA ATA TTC AAA CGG AGG GAG ACG      286
            PENPR2- TAT AAG TTT GCC TCC CTC TG
                     -22                                             334
                     Met Lys Tyr Leu Leu Gly Leu Leu Leu
ATT TTG AAA TAC CTA TTG GGA TTA TTA
            Nco I  VL
Leu Ala Ala Gln Pro Ala Met Ala Asp Ile Val Met Ser Gln Ser Pro      382
CTC GCT GCC CAA CCA ATG GCC GAC ATT GTG ATG TCA CAG TCT CCA
            10                                20
Ser Ser Leu Pro Val Ser Val Gly Glu Lys Val Thr Leu Ser Cys Lys      430
TCC TCC CTA CCT GTG TCA GTT GGC GAG AAG GTT ACT TTG AGC TGC AAG
            30                                40
Ser Ser Gln Ser Leu Leu Tyr Ser Gly Asn Gln Lys Asn Tyr Leu Ala      478
TCC AGT CAG AGC CTT TTA TAT AGT GGT AAT CAA AAG AAC TAC TTG GCC
```

FIG.6B

```
         50
Trp Tyr Gln Gln Lys Pro Gly Gln Ser Pro Lys Leu Leu Ile Tyr Trp       526
TGG TAC CAG CAG AAA CCA GGG CAG TCT CCT AAA CTG CTG ATT TAC TGG
                60                                          70
Ala Ser Ala Arg Glu Ser Gly Val Pro Asp Arg Phe Thr Gly Ser Gly       574
GCA TCC GCT AGG GAA TCT GGG GTC CCT GAT CGC TTC ACA GGC AGT GGA
                                80
Ser Gly Thr Asp Phe Thr Leu Ser Ile Ser Ser Val Lys Thr Glu Asp       622
TCT GGG ACA GAT TTC ACT CTC TCC ATC AGC AGT GTG AAG ACT GAA GAC
                                            100
Leu Ala Val Tyr Tyr Cys Gln Gln Tyr Tyr Ser Tyr Pro Leu Thr Phe       670
CTG GCA GTT TAT TAC TGT CAG CAG TAT TAT AGC TAT CCC CTC ACG TTC
        90                              Hind III           120
Gly Ala Gly Thr Lys Leu Val Leu Lys Leu Ser Ala Asp Asp Ala Lys       718
GGT GCT GGG ACC AAG CTG GTG CTG AAG CTT AGT GCG GAT GAT GCG AAA
                            130
Lys Asp Ala Ala Lys Lys Asp Asp Ala Lys Lys Asp Asp Ala Lys Lys       766
AAG GAT GCT GCG AAG AAG GAT GAC GCT AAG AAG GAT GAT GCT AAA AAG
```

FIG.6C

```
    VH
    Xho I    140                                         150
    Asp Leu Glu Val Gln Leu Gln Gln Ser Asp Ala Glu Leu Val Lys Pro
    GAC CTC GAG GTT CAG TTG CAG CAG TCT GAC GCT GAG TTG GTG AAA CCT    814

160
    Gly Ala Ser Val Lys Ile Ser Cys Lys Ala Ser Gly Tyr Thr Phe Thr
    GGG GCT TCA GTG AAG ATT TCC TGC AAG GCT TCT GGC TAC ACC TTC ACT    862

170                                  180
    Asp His Ala Ile His Trp Val Lys Gln Asn Pro Glu Gln Gly Leu Glu
    GAC CAT GCA ATT CAC TGG GTG AAA CAG AAC CCT GAA CAG GGC CTG GAA    910

190        CC49VHP-                 200
    Trp Ile Gly Tyr Phe Ser Pro Gly Asn Asp Asp Phe Lys Tyr Asn Glu
    TGG ATT GGA TAT TTT TCT CCC GGA AAT GAT GAT TTT AAA TAC AAT GAG    958

210
    Arg Phe Lys Gly Lys Ala Thr Leu Thr Ala Asp Lys Ser Ser Ser Thr
    AGG TTC AAG GGC AAG GCC ACA CTG ACT GCA GAC AAA TCC TCC AGC ACT    1006

220                              230
    Ala Tyr Val Gln Leu Asn Ser Leu Thr Ser Glu Asp Ser Ala Val Tyr
    GCC TAC GTG CAG CTC AAC AGC CTG ACA TCT GAG GAT TCT GCA GTG TAT    1054
```

FIG. 6D

```
                                            240
        VH49J- G AAT ATG GCC TAC TGG GGT CAA G                          1102
                 Asn Met Ala Tyr Trp Gly Gln
Phe Cys Thr Arg Ser Leu                      Gly Thr Ser
TTC TGT ACA AGA TCC CTG AAT ATG GCC TAC TGG GGT CAA GGA ACC TCA
            250                                          260
Val Thr Val Ser Ser Leu Ser Ala Asp Asp Ala Lys Asp Ala Ala         1150
GTC ACC GTC TCC TCA AGC GCA GAT GAC GCA AAG GAC GCA GCT
                            270                        VL  280
Lys Lys Asp Ala Lys Lys Asp Ala Ala Lys Lys Asp Asp Leu Asp Ile     1198
AAA AAG GAT GCC AAA AAG GAC GCC AAG AAA GAT CTT GAC ATT
Val Met Ser Gln Ser Pro Ser Ser Leu Pro Val Ser Val Gly Glu Lys     1246
GTG ATG TCA CAG TCT CCA TCC CTA CCT GTG TCA GTT GGC GAG AAG
            300                     290                  310
Val Thr Leu Ser Cys Lys Ser Ser Gln Ser Leu Leu Tyr Ser Gly Asn     1294
GTT ACT TTG AGC TGC AAG TCC AGT CAG AGC CTT TTA TAT AGT GGT AAT
                                    320
Gln Lys Asn Tyr Leu Ala Trp Tyr Gln Gln Lys Pro Gly Gln Ser Pro     1342
CAA AAG AAC TAC TTG GCC TGG TAC CAG CAG AAA CCA GGG CAG TCT CCT
```

FIG. 6E

```
                        330
Lys Leu Leu Ile Tyr Trp Ala Ser Ala Arg Glu Ser Gly Val Pro Asp
AAA CTG CTG ATT TAC TGG GCA TCC GCT AGG GAA TCT GGG GTC CCT GAT      1390

350                                      360
Arg Phe Thr Gly Ser Gly Ser Gly Thr Asp Phe Thr Leu Ser Ile Ser
CGC TTC ACA GGC AGT GGA TCT GGG ACA GAT TTC ACT CTC TCC ATC AGC      1438

370
                                49VLCDR3+-- Gln Gln Tyr Tyr
Ser Val Lys Thr Glu Asp Leu Ala Val Tyr Tyr Cys Gln Gln Tyr Tyr
AGT GTG AAG ACT GAA GAC CTG GCA GTT TAT TAC TGT CAG CAG TAT TAT      1486

AGC TAT              380                                     390
Ser Tyr Pro Leu Thr Phe Gly Ala Gly Thr Lys Leu Val Leu Lys Leu
AGC TAT CCC CTC ACG TTC GGT GCT GGG ACC AAG CTG GTG CTG AAG CTA      1534

Eco47 III                400
Ser Ala Asp Asp Ala Lys Lys Asp Ala Ala Lys Lys Asp Asp Ala Lys
AGC GCT GAT GAT GCA AAG AAG GAT GCA GCC AAA AAG GAC GAC GCA AAA      1582

VH       420
Lys Asp Asp Ala Lys Lys Asp Leu Glu Val Gln Leu Gln Gln Ser Asp
AAG GAT GAT GCA AAG AAG GAT CTG GAG GTT CAG CTG CAG CAG TCT GAC      1630

430                                          440
Ala Glu Leu Val Lys Pro Gly Ala Ser Val Lys Ile Ser Cys Lys Ala
GCT GAG TTG GTG AAA CCT GGG GCT TCA GTG AAG ATT TCC TGC AAG GCT      1678
```

FIG.6F

| | | | | | | | | | | | | | | | |
|---|---|---|---|---|---|---|---|---|---|---|---|---|---|---|---|
| Ser | Gly | Tyr | Thr | Phe | Thr | Asp | His | Ala | Ile | His | Trp | Val | Lys | Gln | Asn |
| TCT | GGC | TAC | ACC | TTC | ACT | GAC | CAT | GCA | ATT | CAC | TGG | GTG | AAA | CAG | AAC |

1726

450

| | | | | | | | | | | | | | | | |
|---|---|---|---|---|---|---|---|---|---|---|---|---|---|---|---|
| Pro | Glu | Gln | Gly | Leu | Glu | Trp | Ile | Gly | Tyr | Phe | Ser | Pro | Gly | Asn | Asp |
| CCT | GAA | CAG | GGC | CTG | GAA | TGG | ATT | GGA | TAT | TTT | TCT | CCC | GGA | AAT | GAT |

1774

460            470

| | | | | | | | | | | | | | | | |
|---|---|---|---|---|---|---|---|---|---|---|---|---|---|---|---|
| Asp | Phe | Lys | Tyr | Asn | Glu | Arg | Phe | Lys | Gly | Lys | Ala | Thr | Leu | Thr | Ala |
| GAT | TTT | AAA | TAC | AAT | GAG | AGG | TTC | AAG | GGC | AAG | GCC | ACA | CTG | ACT | GCA |

1822

480

| | | | | | | | | | | | | | | | |
|---|---|---|---|---|---|---|---|---|---|---|---|---|---|---|---|
| Asp | Lys | Ser | Ser | Ser | Thr | Ala | Tyr | Val | Gln | Leu | Asn | Ser | Leu | Thr | Ser |
| GAC | AAA | TCC | TCC | AGC | ACT | GCC | TAC | GTG | CAG | CTC | AAC | AGC | CTG | ACA | TCT |

1870

490            500

| | | | | | | | | | | | | | | | |
|---|---|---|---|---|---|---|---|---|---|---|---|---|---|---|---|
| Glu | Asp | Ser | Ala | Val | Tyr | Phe | Cys | Thr | Arg | Ser | Leu | Asn | Met | Ala | Tyr |
| GAG | GAT | TCT | GCA | GTG | TAT | TTC | TGT | ACA | AGA | TCC | CTG | AAT | ATG | GCC | TAC |

1918

510            520

| | | | | | | | | | | |
|---|---|---|---|---|---|---|---|---|---|---|
| Trp | Gly | Gln | Gly | Thr | Ser | Val | Thr | Val | Ser | Ser | *** | Nhe I | | | |
| TGG | GGT | CAA | GGA | ACC | TCA | GTC | ACC | GTC | TCC | TCA | TAA | AAA | GCT | AGC | GAT |

```
GAA TCC GTC AAA ACA TCA TCT TAC ATA AAG TCA CTT GGT GAT CAA GCT
        SQP1- TGT AGT AGA ATG TAT TTC AGT
              PENPTSEQ2- G TAT TTC AGT GAA CCA CTA GTT           2014

CAT ATC ATT GTC CGG CAA TGG TGT GGG CTT TTT TTG TTT TCT ATC TTT   2062

AAA GAT CAT GTG AAG AAA AAC GGG AAA ATC GGT CTG CGG GAA AGG ACC   2110

GGG TTT TTG TCG AAA TCA TAG GCG AAT GGG TTG GAT TGT GAC AAA ATT   2158

BamH I
CGG ATC C-3'                                                      2165
```

FIG.7A

DNA AND AMINO ACID SEQUENCE OF CC49 VL-L-VH-L-VH-L-VL

```
                    Cla I           EcoR I
5'-C TCA TGT TTG ACA GCT TAT CAT CGA TGA ATT CCA TCA CTT CCC TCC        46

GTT CAT TTG TCC CCG GTG GAA ACG AGG TCA TCA TTT CCT TCC GAA AAA         94

ACG GTT GCA TTT AAA TCT TAC ATA TAT AAT ACT TTC AAA GAC TAC ATT        142

TGT AAG ATT TGA TGT TGT TTG AGT CGG CTG AAA GAT CGT ACG CAA TTA        190

PENPR1-  AAC ACT GTA GGG ATA GTG GAA
TTG TTT CGT GAT TGT TCA AGC CAT AAC ACT GTA GGG ATA GTG GAA AGA        238

GTG CTT CAT CTG GTT ACG ATC AAT CAA ATA TTC AAA CGG AGG GAG ACG        286
                           PENPR2- TAT AAG TTT GCC TCC CTC TG

-22
    Met Lys Tyr Leu Leu Pro Thr Ala Ala Gly Leu Leu Leu
ATT TTG ATG AAA TAC CTA TTG CCT ACG GCA GCT GGA TTG TTA TTA            334

Nco I     VL
            Met Ala Met Ala Asp Ile Val Met Ser Gln Ser Pro
CTC GCT GCC CAA CCA ATG GCC ATG GCT GAC ATT GTG TCA CAG TCT CCA        382
                                                    20
Ser Ser Leu Pro Val Ser Val Gly Glu Lys Val Thr Leu Ser Cys Lys
TCC TCC CTA CCT GTG TCA GTT GGC GAG AAG GTT ACT TTG AGC TGC AAG        430
  10
```

FIG.7B

```
     Ser Ser Gln Ser Leu Tyr Ser Gly Asn Gln Lys Asn Tyr Leu Ala
                        30                              40
     TCC AGT CAG AGC CTT TAT AGT GGT AAT CAA AAG AAC TAC TTG GCC    478

Trp Tyr Gln Lys Pro Gly Gln Ser Pro Lys Leu Leu Ile Tyr Trp
                                     50
     TGG TAC CAG AAA CCA GGG CAG TCT CCT AAA CTG CTG ATT TAC TGG    526

Ala Ser Ala Arg Glu Ser Gly Val Pro Asp Arg Phe Thr Gly Ser Gly
             60                                      70
     GCA TCC GCT AGG GAA TCT GGG GTC CCT GAT CGC TTC ACA GGC AGT GGA    574

Ser Gly Thr Asp Phe Thr Leu Ser Ile Ser Ser Val Lys Thr Glu Asp
                                 80
     TCT GGG ACA GAT TTC ACT CTC TCC ATC AGC AGT GTG AAG ACT GAA GAC    622

Leu Ala Val Tyr Tyr Cys Gln Gln Tyr Tyr Ser Tyr Pro Leu Thr Phe
             90                                          100
     CTG GCA GTT TAT TAC TGT CAG CAG TAT TAT AGC TAT CCC CTC ACG TTC    670

Hind III
     Gly Ala Gly Thr Lys Leu Val Leu Lys Leu Ser Ala Asp Ala Lys
                                 110                          120
     GGT GCT GGG ACC AAG CTG GTG CTG AAG CTT AGT GCG GAT GCG AAA    718

Lys Asp Asp Ala Ala Lys Lys Asp Asp Ala Lys Lys Asp Asp Ala Lys Lys
                                             130
     AAG GAT GAT GCG GCG AAG AAG GAC GAT GCT AAA AAG GAC GAT GCT AAA AAG
     TTC CTA CTA CGC CGC TTC TTC CTA CTA TMNVL(-)SEQ                    766
```

FIG. 7C

```
        VH
        I    140                                              150
   Xho  Leu  Glu  Val  Gln  Leu  Gln  Ser  Asp  Ala  Glu  Leu  Val  Lys  Pro
   Asp  CTC  GAG  GTT  CAG  TTG  CAG  TCT  GAC  GCT  GAG  TTG  GTG  AAA  CCT   814
   GAC

160
   Gly  Ala  Ser  Val  Lys  Ile  Ser  Cys  Lys  Ala  Ser  Gly  Tyr  Phe  Thr
   GGG  GCT  TCA  GTG  AAG  ATT  TCC  TGC  AAG  GCT  TCT  GGC  TAC  TTC  ACT   862

170                                      180
   Asp  His  Ala  Ile  His  Trp  Val  Lys  Gln  Asn  Pro  Glu  Gln  Gly  Leu  Glu
   GAC  CAT  GCA  ATT  CAC  TGG  GTG  AAA  CAG  AAC  CCT  GAA  CAG  GGC  CTG  GAA   910

190      CC49VHP-                            200
   Trp  Ile  Gly  Tyr  Phe  Ser  Pro  Gly  Asn  Asp  Asp  Phe  Lys  Tyr  Asn  Glu
   TGG  ATT  GGA  TAT  TTT  TCT  CCC  GGA  AAT  GAT  GAT  TTT  AAA  TAC  AAT  GAG   958

Arg  Phe  Lys  Gly  Lys  Ala  Thr  Leu  Thr  Ala  Asp  Lys  Ser  Ser  Ser  Thr
   AGG  TTC  AAG  GGC  AAG  GCC  ACA  CTG  ACT  GCA  GAC  AAA  TCC  TCC  AGC  ACT   1006

220                               210            230
   Ala  Tyr  Val  Gln  Leu  Asn  Ser  Leu  Thr  Ser  Glu  Asp  Ser  Ala  Val  Tyr
   GCC  TAC  GTG  CAG  CTC  AAC  AGC  CTG  ACA  TCT  GAG  GAT  TCT  GCA  GTG  TAT   1054

240    VH49J-   G
   Phe  Cys  Thr  Arg  Ser  Leu  Asn  Met  Ala  Tyr  Trp  Gly  Gln  Gly  Thr  Ser
   TTC  TGT  ACA  AGA  TCC  CTG  AAT  ATG  GCC  TAC  TGG  GGT  CAA  GGA  ACC  TCA   1102
```

FIG.7D

```
    250
Val Thr Val Ser Ser Leu Ser Ala Asp Ala Lys Lys Asp Ala Ala      1150
GTC ACC GTC TCC TCA CTA AGC GCA GAT GCA AAG AAA GAC GCA GCT
                                                  VH  280
        270
Lys Lys Asp Ala Lys Lys Asp Ala Asp Ala Lys Lys Asp Leu Val      1198
AAA AAA GAC GCC AAA AAG GAT GAC GCC AAG AAA GAT CTT GAG GTT
                              290
Gln Leu Gln Ser Asp Ala Glu Leu Val Lys Pro Gly Ala Ser Val      1246
CAG TTG CAG TCT GAC GCT GAG TTG GTG AAA CCT GGG GCT TCA GTG
            300                               310
Lys Ile Ser Cys Lys Ala Ser Gly Tyr Thr Phe Thr Asp His Ala Ile  1294
AAG ATT TCC TGC AAG GCT TCT GGC TAC ACC TTC ACT GAC CAT GCA ATT
                          320
His Trp Val Lys Gln Asn Pro Glu Gln Gly Leu Glu Trp Ile Gly Tyr  1342
CAC TGG GTG AAA CAG AAC CCT GAA CAG GGC CTG GAA TGG ATT GGA TAT
        330                           340
Phe Ser Pro Gly Asn Asp Asp Phe Lys Tyr Asn Glu Arg Phe Lys Gly  1390
TTT TCT CCC GGA AAT GAT GAT TTT AAA TAC AAT GAG AGG TTC AAG GGC
                              350                               360
Lys Ala Thr Leu Thr Ala Asp Lys Ser Ser Ser Thr Ala Tyr Val Gln  1438
AAG GCC ACA CTG ACT GCA GAC AAA TCC AGC AGC ACT GCC TAC GTG CAG
                      370
Leu Asn Ser Leu Thr Ser Glu Asp Ser Ala Val Tyr Phe Cys Thr Arg  1486
CTC AAC AGC CTG ACA TCT GAG GAT TCT GCA GTG TAT TTC TGT ACA AGA
```

FIG. 7E

```
                380                                       390
Ser Leu Asn Met Ala Tyr Trp Gly Gln Gly Thr Ser Val Thr Val Ser
TCC CTG AAT ATG GCC TAC TGG GGT CAA GGA ACC TCA GTC ACC GTC TCC    1534

400
Ser Leu Ser Ala Asp Asp Ala Lys Lys Asp Ala Ala Lys Lys Asp Asp
TCA CTA AGC GCA GAT GAC GCA AAG AAA GAC GCA GCT AAA AAA GAC GAT   1582

410                               VL  420
Ala Lys Lys Asp Asp Ala Lys Lys Asp Leu Asp Ile Val Met Ser Gln
GCC AAA AAG GAT GAC GCC AAG AAA GAT CTT GAC ATT GTG ATG TCA CAG   1630

430                                       440
Ser Pro Ser Ser Leu Pro Val Ser Val Gly Glu Lys Val Thr Leu Ser
TCT CCA TCC TCC CTA CCT GTG TCA GTT GGC GAG AAG GTT ACT TTG AGC   1678

450
Cys Lys Ser Ser Gln Ser Leu Leu Tyr Ser Gly Asn Gln Lys Asn Tyr
TGC AAG TCC AGT CAG AGC CTT TTA TAT AGT GGT AAT CAA AAG AAC TAC   1726
                                                          49LFR2(-)- G 460                                   470
Leu Ala Trp Tyr Gln Gln Lys Pro Gly Gln Ser Pro Lys Leu Leu Ile
TTG GCC TGG TAC CAG CAG AAA CCA GGG CAG TCT CCT AAA CTG CTG ATT   1774
AAC CGG ACC ATG GTC GTC

480
Tyr Trp Ala Ser Ala Arg Glu Ser Gly Val Pro Asp Arg Phe Thr Gly
TAC TGG GCA TCC GCT AGG GAA TCT GGG GTC CCT GAT CGC TTC ACA GGC   1822
```

FIG. 7F

```
      490
Ser Gly Ser Gly Thr Asp Phe Thr Leu Ser Ile Ser Val Lys Thr
AGT GGA TCT GGG ACA GAT TTC ACT CTC TCC ATC AGC AGT GTG AAG ACT        1870
                        510                              520
Glu Asp Leu Ala Val Tyr Tyr Cys Gln Gln Tyr Tyr Ser Tyr Pro Leu
GAA GAC CTG GCA GTT TAT TAC TGT CAG CAG TAT TAT AGC TAT CCC CTC        1918
                        530
                        Afl II                  Nhe I
Thr Phe Gly Ala Gly Thr Lys Leu Val Leu Lys ***
ACG TTC GGT GCT GGG ACC AAG CTG GTG CTT AAG TAA AAA GCT AGC GAT        1966

GAA TCC GTC AAA ACA TCA TCT TAC ATA AAG TCA CTT GGT GAT CAA GCT        2014
    SQP1- TGT AGT AGA ATG TAT TTC AGT
         PENPTSEQ2- G TAT TTC AGT GAA CCA CTA GTT

CAT ATC ATT GTC CGG CAA TGG TGT GGG CTT TTT TCT ATC TTT               2062

AAA GAT CAT GTG AAG AAA AAC GGG AAA ATC GGT CTG CGG GAA AGG ACC        2110

GGG TTT TTG TCG AAA TCA TAG GCG AAT GGG TTG GAT TGT GAC AAA ATT       2158

BamH I
CGG ATC C-3'                                                           2165
```

MULTIVALENT SINGLE CHAIN ANTIBODIES

CROSS-REFERENCE TO RELATED APPLICATION

This is a divisional of application Ser. No. 08,263,911 filed Jun. 21, 1994, which is a Continuation-in-Part of application Ser. Number 07/990,263 filed Dec. 11, 1992, now abandoned.

BACKGROUND OF THE INVENTION

The present invention relates to single chain multivalent antibodies.

Antibodies are proteins belonging to a group of immunoglobulins elicited by the immune system in response to a specific antigen or substance which the body deems foreign. There are five classes of human antibodies, each class having the same basic structure. The basic structure of an antibody is a tetramer, or a multiple thereof, composed of two identical heterodimers each consisting of a light and a heavy chain. The light chain is composed of one variable (V) and one constant (C) domain, while a heavy chain is composed of one variable and three or more constant domains. The variable domains from both the light and heavy chain, designated $V_L$ and $V_H$ respectively, determine the specificity of an immunoglobulin, while the constant (C) domains carry out various effector functions.

Amino acid sequence data indicate that each variable domain comprises three complementarity determining regions (CDR) flanked by four relatively conserved framework regions (FR). The FR are thought to maintain the structural integrity of the variable region domain. The CDR have been assumed to be responsible for the binding specificity of individual antibodies and to account for the diversity of binding of antibodies.

As the basic structure of an antibody contains two heterodimers, antibodies are multivalent molecules. For example, the IgG classes have two identical antigen binding sites, while the pentameric IgM class has 10 identical binding sites.

Monoclonal antibodies having identical genetic parentage and binding specificity have been useful both as diagnostic and therapeutic agents. Monoclonal antibodies are routinely produced by hybridomas generated by fusion of mouse lymphoid cells with an appropriate mouse myeloma cell line according to established procedures. The administration of murine antibodies for in vivo therapy and diagnostics in humans is limited however, due to the human anti-mouse antibody response illicited by the human immune system.

Chimeric antibodies, in which the binding or variable regions of antibodies derived from one species are combined with the constant regions of antibodies derived from a different species, have been produced by recombinant DNA methodology. See, for example, Sahagen et al., *J. Immunol.* 137:1066–1074 (1986); Sun et al., *Proc. Natl. Acad. Sci. USA*, 82:214–218 (1987); Nishimura et al., *Cancer Res.* 47:999–1005 (1987); and Lie et al. *Proc Natl. Acad. Sci. USA*, 84:3439–3443 (1987) which disclose chimeric antibodies to tumor-associated antigens. Typically, the variable region of a murine antibody is joined with the constant region of a human antibody. It is expected that as such chimeric antibodies are largely human in composition, they will be substantially less immunogenic than murine antibodies.

Chimeric antibodies still carry the Fc regions which are not necessary for antigen binding, but constitute a major portion of the overall antibody structure which affects its pharmacokinetics. For the use of antibodies in immunotherapy or immunodiagnostics, is it desirable to have antibody-like molecules which localize and bind to the target tissue rapidly and for the unbound material to quickly clear from the body. Generally, smaller antibody fragments have greater capillary permeability and are more rapidly cleared from the body than whole antibodies.

Since it is the variable regions of light and heavy chains that interact with an antigen, single chain antibody fragments (scFvs) have been created with one $V_L$ and one $V_H$, containing all six CDR's, joined by a peptide linker (U.S. Pat. No. 4,946,778) to create a $V_L$-L-$V_H$ polypeptide, wherein the L stands for the peptide linker. A scFv wherein the $V_L$ and $V_H$ domains are orientated $V_H$-L-$V_L$ is disclosed in U.S. Pat. No. 5,132,405.

As the scFvs have one binding site as compared to the minimum of two for complete antibodies, the scFvs have reduced avidity as compared to the antibody containing two or more binding sites.

It would therefore be advantageous to obtain constructions of scFvs having more than one binding site to enhance the avidity of the polypeptide, and retain or increase their antigen recognition properties. In addition it would be beneficial to obtain multivalent scFvs which are bispecific to allow for recognition of different epitopes on the target tissue, to allow for antibody-based recruitment of other immune effector functions, or allow antibody capture of a therapeutic or diagnostic moiety.

SUMMARY OF THE INVENTION

It has been found that single chain antibody fragments, each having one $V_H$ and one $V_L$ domain covalently linked by a first peptide linker, can be covalently linked by a second peptide linker to form a multivalent single chain antibody which maintains the binding affinity of a whole antibody. In one embodiment, the present invention is a multivalent single chain antibody having affinity for an antigen wherein the multivalent single chain antibody comprises two or more light chain variable domains and two or more heavy chain variable domains; wherein each variable domain is linked to at least one other variable domain.

In another embodiment, the present invention is a multivalent single chain antibody which comprises two or more single chain antibody fragments, each fragment having affinity for an antigen wherein the fragments are covalently linked by a first peptide linker and each fragment comprising (a) a first polypeptide comprising a light chain variable domain; (b) a second polypeptide comprising a heavy chain variable domain; and (c) a second peptide linker linking the first and second polypeptides into a functional binding moiety.

In another embodiment, the invention provides a DNA sequence which codes for a multivalent single chain antibody, the multivalent single chain antibody comprising two or more single chain antibody fragments, each fragment having affinity for an antigen wherein the fragments are covalently linked by a first peptide linker and each fragment comprising (a) a first polypeptide comprising a light chain variable domain; (b) a second polypeptide comprising a heavy chain variable domain; and (c) a second peptide linker linking the first and second polypeptides into a functional binding moiety.

The multivalent single chain antibodies allow for the construction of an antibody fragment which has the specificity and avidity of a whole antibody but are smaller in size allowing for more rapid capillary permeability. Multivalent single chain antibodies also allow for the construction of a multivalent single chain antibody wherein the binding sites can be to different antigenic determinants.

BRIEF DESCRIPTION OF THE DRAWINGS

FIG. 1 illustrates, i.e. FIGS. 1—1, 1-2, and 1-3 illustrate covalently linked single chain antibodies having the configuration $V_L$-L-$V_H$-L-$V_L$-L-$V_H$ (LHLH) and $V_L$-L-$V_H$-L-$V_H$-L-$V_L$ (LHHL) and a noncovalently linked Fv single chain antibody (Fv2), respectively.

FIG. 2 illustrates the nucleotide sequence of CC49 $V_L$.

FIG. 3 illustrates the amino acid sequence of CC49 $V_L$.

FIG. 4 illustrates the nucleotide sequence of CC49 $V_H$.

FIG. 5 illustrates the amino acid sequence of CC49 $V_H$.

FIG. 6 illustrates the nucleotide sequence and amino acid sequence of the CC49 single chain antibody LHLH in p49LHLH.

FIG. 7 illustrates the nucleotide sequence and amino acid sequence of the CC49 single antibody LHHL in p49LHHL.

DETAILED DESCRIPTION OF THE INVENTION

Figure 8:
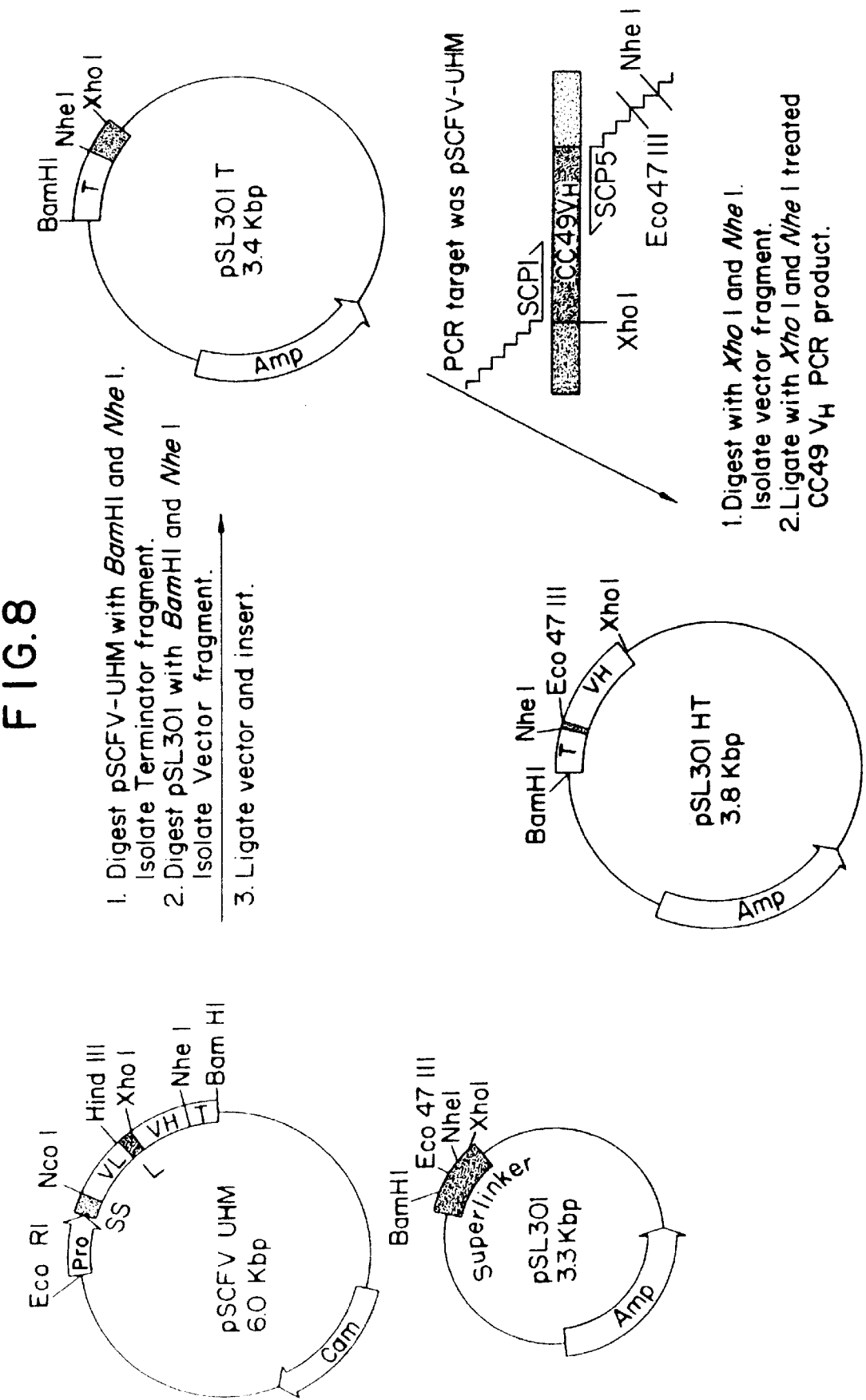
FIG. 8 illustrates construction of plasmids pSL301 T and pSL301 HT.
Figure 9:
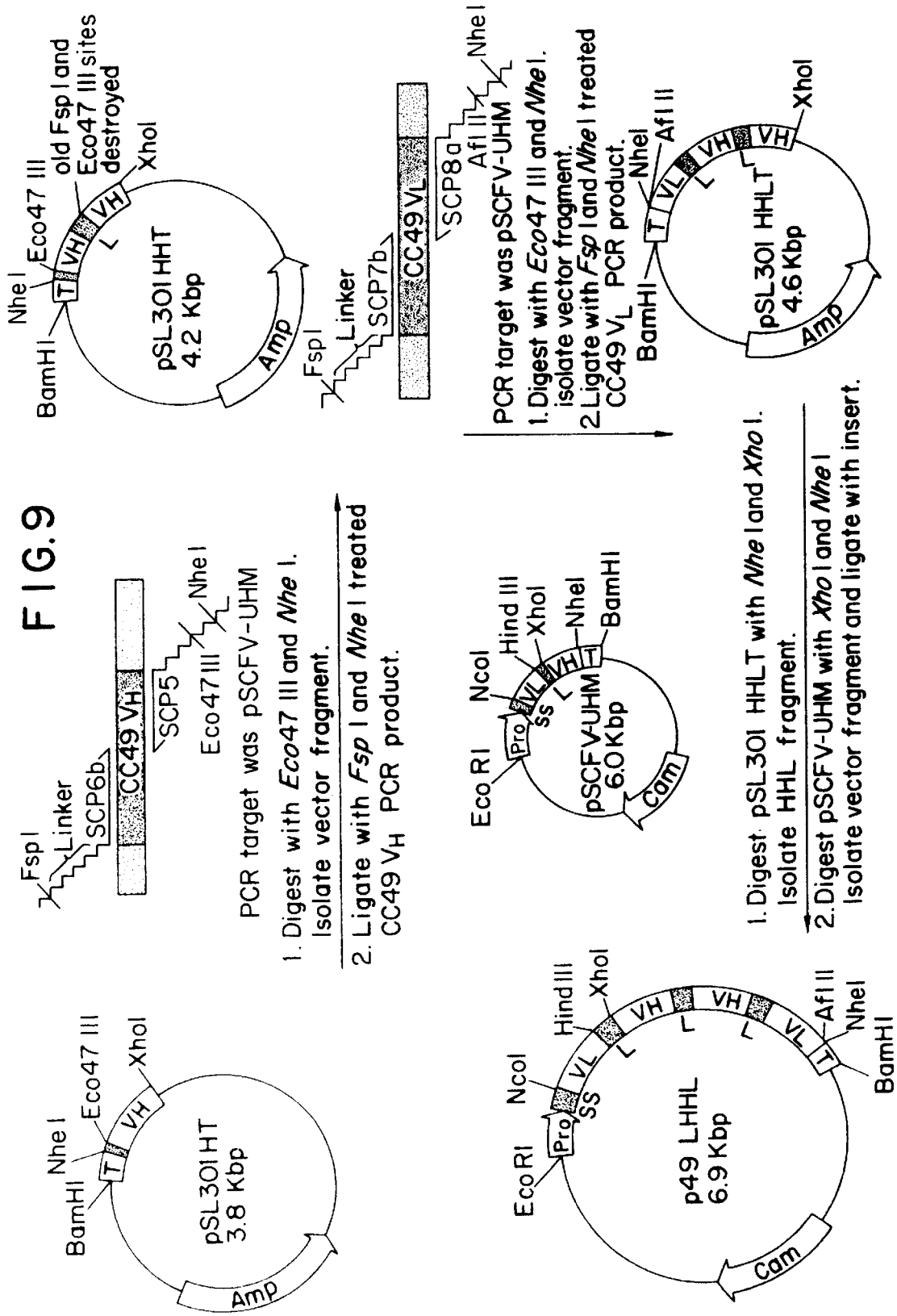
FIG. 9 illustrates construction of plasmid p49LHHL.

The entire teaching of all references cited herein are hereby incorporated by reference.

Nucleic acids, amino acids, peptides, protective groups, active groups and such, when abbreviated, are abbreviated according to the IUPAC IUB (Commission on Biological Nomenclature) or the practice in the fields concerned.

The term "single chain antibody fragment" (scFv) or "antibody fragment" as used herein means a polypeptide containing a $V_L$ domain linked to a $V_H$ domain by a peptide linker (L), represented by $V_L$-L-$V_H$. The order of the $V_L$ and $V_H$ domains can be reversed to obtain polypeptides represented as $V_H$-L-$V_L$. "Domain" is a segment of protein that assumes a discrete function, such as antigen binding or antigen recognition.

A "multivalent single chain antibody" means two or more single chain antibody fragments covalently linked by a peptide linker. The antibody fragments can be joined to form bivalent single chain antibodies having the order of the $V_L$ and $V_H$ domains as follows: $V_L$-L-$V_H$-L-$V_L$-L-$V_H$; $V_L$-L-$V_H$-L-$V_H$-L-$V_L$; $V_H$-L-$V_L$-L-$V_H$-L-$V_L$; or $V_H$-L-$V_L$-L-$V_L$-L-$V_H$. Single chain multivalent antibodies which are trivalent and greater have one or more antibody fragments joined to a bivalent single chain antibody by an additional interpeptide linker. In a preferred embodiment, the number of $V_L$ and $V_H$ domains is equivalent.

The present invention also provides for multivalent single chain antibodies which can be designated $V_H$-L-$V_H$-L-$V_L$-L-$V_L$ or $V_L$-L-$V_L$-L-$V_H$-L-$V_H$.

Covalently linked single chain antibodies having the configuration $V_L$-L-$V_H$-L-$V_L$-L-$V_H$ (LHLH) and $V_L$-L-$V_H$-L-$V_H$-L-$V_L$ (LHHL) are illustrated in FIG. 1. A noncovalently linked Fv single chain antibody (Fv2) is also illustrated in FIG. 1.

The single chain antibody fragments for use in the present invention can be derived from the light and/or heavy chain variable domains of any antibody. Preferably, the light and heavy chain variable domains are specific for the same antigen. The individual antibody fragments which are joined to form a multivalent single chain antibody may be directed against the same antigen or can be directed against different antigens.

To prepare a vector containing the DNA sequence for a single chain multivalent antibody, a source of the genes encoding for these regions is required. The appropriate DNA sequence can be obtained from published sources or can be obtained by standard procedures known in the art. For example, Kabat et al., *Sequences of Proteins of Immunological Interest* 4th ed (1991), published by The U.S. Department of Health and Human Services, discloses sequences of most of the antibody variable regions which have been described to date.

When the genetic sequence is unknown, it is generally possible to utilize cDNA sequences obtained from mRNA by reverse transcriptase mediated synthesis as a source of DNA to clone into a vector. For antibodies, the source of mRNA can be obtained from a wide range of hybridomas. See, for example, the catalogue *ATCC Cell Lines and Hybridomas*, American Type Culture Collection, 20309 Parklawn Drive, Rockville Md., USA (1990). Hybridomas secreting monoclonal antibodies reactive with a wide variety of antigens are listed therein, are available from the collection, and usable in the present invention. These cell lines and others of similar nature can be utilized as a source of mRNA coding for the variable domains or to obtain antibody protein to determine amino acid sequence of the monoclonal antibody itself.

Variable regions of antibodies can also be derived by immunizing an appropriate vertebrate, normally a domestic animal, and most conveniently a mouse. The immunogen will be the antigen of interest, or where a hapten, an antigenic conjugate of the hapten to an antigen such as keyhole limpet hemocyanin (KLH). The immunization may be carried out conventionally with one or more repeated injections of the immunogen into the host mammal, normally at two to three week intervals. Usually three days after the last challenge, the spleen is removed and dissociated into single cells to be used for cell fusion to provide hybridomas from which mRNA can readily be obtained by standard procedures known in the art.

When an antibody of interest is obtained, and only its amino acid sequence is known, it is possible to reverse translate the sequence.

The $V_L$ and $V_H$ domains for use in the present invention are preferably obtained from one of a series of CC antibodies against tumor-associated glycoprotein 72 antigen (TAG-72) disclosed in published PCT Application WO 90/04410 on May 3, 1990, and published PCT Application WO 89/00692 on Jan. 26, 1989. More preferred are the $V_L$ and $V_H$ domains from the monoclonal antibody designated CC49 in PCT Publications WO 90/04410 and WO 89/00692. The nucleotide sequence (SEQ ID NO: 1) which codes for the $V_L$ of CC49 is substantially the same as that given in FIG. 2. The amino acid sequence (SEQ ID NO: 2) of the $V_L$ of CC49 is substantially the same as that given in FIG. 3. The nucleotide sequence (SEQ ID NO: 3) which codes for the $V_H$ of CC49 is substantially the same as that given in FIG. 4. The amino acid sequence (SEQ ID NO: 4) for the $V_H$ of CC49 is substantially the same as that given in FIG. 5.

To form the antibody fragments and multivalent single chain antibodies of the present invention, it is necessary to have a suitable peptide linker. Suitable linkers for joining the $V_H$ and $V_L$ domains are those which allow the $V_H$ and $V_L$ domains to fold into a single polypeptide chain which will have a three dimensional structure very similar to the original structure of a whole antibody and thus maintain the binding specificity of the whole antibody from which antibody fragment is derived. Suitable linkers for linking the scFvs are those which allow the linking of two or more scFvs such that the $V_H$ and $V_L$ domains of each immunoglobulin fragment have a three dimensional structure such that each fragment maintains the binding specificity of the whole antibody from which the immunoglobulin fragment is derived. Linkers having the desired properties can be obtained by the method disclosed in U.S. Pat. No. 4,946,778, the disclosure of which is hereby incorporated by reference. From the polypeptide sequences generated by the methods described in the 4,946,778, genetic sequences coding for the polypeptide can be obtained.

Preferably, the peptide linker joining the VH and $V_L$ domains to form a scFv and the peptide linker joining two or more scFvs to form a multivalent single chain antibody have substantially the same amino acid sequence.

It is also necessary that the linker peptides be attached to the antibody fragments such that the binding of the linker to the individual antibody fragments does not interfere with the binding capacity of the antigen recognition site.

A preferred linker is based on the helical linker designated 205C as disclosed in Pantoliano et al. *Biochem.*, 30, 10117–10125 (1991) but with the first and last amino acids changed because of the codon dictated by the Xho I site at one end and the Hind III site at the other. The amino acid sequence (SEQ ID NO: 5) of the preferred linker is as follows: Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu.

The linker is generally about 10 to about 50 amino acid residues. Preferably the linker is about 10 to about 30 amino acid residues. More preferably the linker is about 12 to about 30 amino acid residues. Most preferred is a linker of about 15 to about 25 amino acid residues.

Expression vehicles for production of the molecules of the invention include plasmids or other vectors. In general, such vectors contain replicon and control sequences which are derived from species compatible with a host cell. The vector ordinarily carries a replicon site, as well as specific genes which are capable of providing phenotypic selection in transformed cells. For example, *E. coli* is readily transformed using pBR322 [Bolivar et al., *Gene*, 2, 95-(1977), or Sambrook et al., *Molecular Cloning*, Cold Spring Harbor Press, New York, 2nd Ed. (1989)].

Plasmids suitable for eukaryotic cells may also be used. *S. cerevisiae*, or common baker's yeast, is the most commonly used among eukaryotic microorganisms although a number of other strains, such as *Pichia pastoris*, are available. Cultures of cells derived from multicellular organisms such as SP2/0 or Chinese Hamster Ovary (CHO), which are available from the ATCC, may also be used as hosts. Typical of vector plasmids suitable for mammalian cells are pSV2neo and pSV2gpt (ATCC); pSVL and pKSV-10 (Pharmacia), pBPV-1/pML2d (International Biotechnology, Inc.).

The use of prokaryotic and eukaryotic viral expression vectors to express the genes for polypeptides of the present invention is also contemplated.

It is preferred that the expression vectors and the inserts which code for the single chain multivalent antibodies have compatible restriction sites at the insertion junctions and that those restriction sites are unique to the areas of insertion. Both vector and insert are treated with restriction endonucleases and then ligated by any of a variety of methods such as those described in Sambrook et al., supra.

Preferred genetic constructions of vectors for production of single chain multivalent antibodies of the present invention are those which contain a constitutively active transcriptional promoter, a region encoding signal peptide which will direct synthesis/secretion of the nascent single chain polypeptide out of the cell. Preferably, the expression rate is commensurate with the transport, folding and assembly steps to avoid accumulation of the polypeptide as insoluble material. In addition to the replicon and control sequences, additional elements may also be needed for optimal synthesis of single chain polypeptide. These elements may include splice signals, as well as transcription promoter, enhancers, and termination signals. Furthermore, additional genes and their products may be required to facilitate assembly and folding (chaperones).

Vectors which are commercially available can easily be altered to meet the above criteria for a vector. Such alterations are easily performed by those of ordinary skill in the art in light of the available literature and the teachings herein.

Additionally, it is preferred that the cloning vector contain a selectable marker, such as a drug resistance marker or other marker which causes expression of a selectable trait by the host cell. "Host cell" refers to cells which can be recombinantly transformed with vectors constructed using recombinant DNA techniques. A drug resistance or other selectable marker is intended in part to facilitate in the selection of transformants. Additionally, the presence of a selectable marker, such as a drug resistance marker, may be of use in keeping contaminating microorganisms from multiplying in the culture medium. In this embodiment, such a pure culture of the transformed host cell would be obtained by culturing the cells under conditions which require the induced phenotype for survival.

Recovery and purification of the present invention can be accomplished using standard techniques known in the art. For example, if they are secreted into the culture medium, the single chain multivalent antibodies can be concentrated by ultrafiltration. When the polypeptides are transported to the periplasmic space of a host cell, purification can be accomplished by osmotically shocking the cells, and proceeding with ultrafiltration, antigen affinity column chromatography or column chromatography using ion exchange chromatography and gel filtration. Polypeptides which are insoluble and present as refractile bodies, also called inclusion bodies, can be purified by lysis of the cells, repeated centrifugation and washing to isolate the inclusion bodies, solubilization, such as with guanidine-HCl, and refolding followed by purification of the biologically active molecules.

The activity of single chain multivalent antibodies can be measured by standard assays known in the art, for example competition assays, enzyme-linked immunosorbant assay (ELISA), and radioimmunoassay (RIA).

The multivalent single chain antibodies of the present invention provide unique benefits for use in diagnostics and therapeutics. The use of multivalent single chain antibodies afford a number of advantages over the use of larger fragments or entire antibody molecules. They reach their target tissue more rapidly, and are cleared more quickly from the body.

For diagnostic and/or therapeutic uses, the multivalent single chain antibodies can be constructed such that one or more antibody fragments are directed against a target tissue and one or more antibody fragments are directed against a diagnostic or therapeutic agent.

The invention also concerns pharmaceutical compositions which are particularly advantageous for use in the diagnosis and/or therapy of diseases, such as cancer, where target antigens are often expressed on the surface of cells. For diagnostic and/or therapeutic uses, the multivalent single chain antibodies can be conjugated with an appropriate imaging or therapeutic agent by methods known in the art. The pharmaceutical compositions of the invention are prepared by methods known in the art, e.g. by conventional mixing, dissolving or lyophilizing processes.

The invention will be further clarified by a consideration of the following examples, which are intended to be purely exemplary of the present invention.

| ABBREVIATIONS | |
| --- | --- |
| BCIP | 5-bromo-4-chloro-3-indoyl phosphate |
| bp | base pair |
| Bis-Tris propane | (1,3-bis[tris(hydroxymethyl)-methylamino]-propane) |
| BSA | bovine serum albumin |
| CDR | Complementarity determining region |
| ELISA | enzyme linked immunosorbent assay |
| Fv2 | non-covalent single chain Fv dimer |
| IEF | isoelectric focusing |
| Kbp | kilo base pair |
| LB | Luria-Bertani medium |
| Mab | monoclonal antibody |
| MES | 2-(N-Morpholino)ethane sulfonic acid |
| MW | molecular weight |
| NBT | nitro blue tetrazolium chloride |
| Oligo | Oligonucleotides |
| PAG | polyacrylamide gel |
| PAGE | polyacrylamide gel electrophoresis |
| PBS | phosphate buffered saline |
| PCR | polymerase chain reaction |
| pSCFV | plasmid containing DNA sequence coding for SCFV |
| RIGS | radioimmunoguided surgery |
| RIT | radioimmunotherapy |
| scFv | single chain Fv immunoglobulin fragment monomer |
| scFv2 | single chain Fv immunoglobulin fragment dimer covalently linked |
| SDS | sodium dodecyl sulfate |
| TBS | Tris-buffered saline |
| Tris | (Tris[hydroxymethyl]aminomethane) |
| TTBS | Tween-20 wash solution |
| VH | immunoglobulin heavy chain variable domain |
| VL | immunoglobulin light chain variable domain |

Antibodies

CC49: A murine monoclonal antibody specific to the human tumor-associated glycoprotein 72 (TAG-72) deposited as ATCC No. HB9459.

CC49 FAB: An antigen binding portion of CC49 consisting of an intact light chain linked to the N-terminal portion of the heavy chain.

CC49 scFv: Single chain antibody fragment consisting of two variable domains of CC49 antibody joined by a peptide linker.

CC49 Fv2: Two CC49 scFv non-covalently linked to form a dimer. The number after Fv refers to the number of monomer subunits of a given molecule, e.g., CC49 Fv6 refers to the hexamer multimers.

CC49 scFv2: Covalently-linked single chain antibody fragment consisting of two CC49 $V_L$ domains and two $V_H$ domains joined by three linkers. Six possible combinations for the order of linking the $V_L$(L) and the $V_H$(H) domains together are: LHLH, LHHL, LLHH, HLLH, HLHL, and HHLL.

Plasmids pSCFV UHM: Plasmid containing coding sequence for scFv consisting of a CC49 variable light chain and a CC49 variable heavy chain joined by a 25 amino acid linker.

p49LHLH or p49LHHL: Plasmids containing the coding sequence for producing CC49 scFv2 LHLH or LHHL products, respectively.

EXAMPLES

General Experimental

Procedures for molecular cloning are as those described in Sambrook et al., *Molecular Cloning*, Cold Spring Harbor Press, New York, 2nd Ed. (1989) and Ausubel et al., *Current Protocols in Molecular Biology*, John Wiley and Sons, New York (1992), the disclosures of which are hereby incorporated by reference.

All water used throughout was deionized distilled water.

Oligonucleotide Synthesis and Purification

All oligonuclotides (oligos) were synthesized on either a Model 380A or a Model 391 DNA Synthesizer from Applied Biosystems (Foster City, Calif.) using standard β-cyanoethyl phosphoramidites and synthesis columns. Protecting groups on the product were removed by heating in concentrated ammonium hydroxide at 55° C. for 6 to 15 hours. The ammonium hydroxide was removed through evaporation and the crude mixtures were resuspended in 30 to 40 μL of sterile water. After electrophoresis on polyacrylamide-urea gels, the oligos were visualized using short wavelength ultraviolet (UV) light. DNA bands were excised from the gel and eluted into 1 mL of 100 mM Tris-HCl, pH 7.4, 500 mM NaCl, 5 mM EDTA over 2 hours at 65° C. Final purification was achieved by applying the DNA to Sep-Pac™ C-18 columns (Millipore, Bedford, Mass.) and eluting the bound oligos with 60 percent methanol. The solution volume was reduced to approximately 50 μL and the DNA concentration was determined by measuring the optical density at 260 nm ($OD_{260}$).

Restriction Enzyme Digests

All restriction enzyme digests were performed using Bethesda Research Laboratories (Gaithersburg, Md.), New England Biolabs, Inc. (Beverly, Mass.) or Boehringer Mannheim (BM, Indianapolis, Ind.) enzymes and buffers following the manufacturer's recommended procedures. Digested products were separated by polyacrylamide gel electrophoresis (PAGE). The gels were stained with ethidium bromide, the DNA bands were visualized using long wavelength UV light and the DNA bands were then excised. The gel slices were placed In dialysis tubing (Union Carbide Corp., Chicago) containing 5 mM Tris, 2.5 mM acetic acid, 1 mM EDTA, pH 8.0 and eluted using a Max Submarine electrophoresis apparatus (Hoefer Scientific Instruments, Calif.). Sample volumes were reduced on a Speed Vac Concentrator (Savant Instruments, Inc., NY). The DNA was ethanol precipitated and redissolved in sterile water.

Enzyme Linked Immunosorbent Assay (EL1SA)

TAG-72 antigen, prepared substantially as described by Johnson et al, *Can. Res.*, 46, 850–857 (1986), was adsorbed onto the wells of a polyvinyl chloride 96 well microtiter plate (Dynatech Laboratories, Inc., Chantilly, Va.) by drying overnight. The plate was blocked with 1 percent BSA in PBS for 1 hour at 31° C. and then washed 3 times with 200 μL of PBS, 0.05 percent Tween-20. 25 μL of test antibodies and 25 μL of biotinylated CC49 (1/20,000 dilution of a 1 mg/mL solution) were added to the wells and the plate incubated for 30 minutes at 31° C. The relative amounts of TAG-72 bound to the plate, biotinylated CC49, streptavidin-alkaline phosphatase, and color development times were determined empirically in order not to have excess of either antigen or biotinylated CC49, yet have enough signal to detect competition by scFv. Positive controls were CC49 at 5 µg/mL and CC49 Fab at 10 µg/mL. Negative controls were 1 percent BSA in PBS and/or concentrated LB. Unbound proteins were washed away. 50 µL of a 1:1000 dilution of streptavidin conjugated with alkaline phosphatase (Southern Biotechnology Associates, Inc., Birmingham, Ala.) were added and the plate was incubated for 30 minutes at 31° C. The plate was washed 3 more times. 50 µL of a para-nitrophenyl-phosphate solution (Kirkegaard & Perry Laboratories, Inc., Gaithersburg, Md.) were added and the color reaction was allowed to develop for a minimum of 20 minutes. The relative amount of scFv2 binding was measured by optical density scanning at 404–450 nm using a microplate reader (Molecular Devices Corporation, Manlo Park, Calif.). Binding of the scFv2 species resulted in decreased binding of the biotinylated CC49 with a concomitant decrease in color development.

SDS-PAGE and Western Blotting

Samples for SDS-PAGE analysis (20 µL) were prepared by boiling in a non-reducing sample preparation buffer-Seprasol I (Integrated Separation Systems (ISS), Natick, Mass.) for 5 minutes and loaded on 10–20 percent gradient polyacrylamide Daiichi Minigels as per the manufacturer's directions (ISS).

Electrophoresis was conducted using a Mini 2-gel apparatus (ISS) at 55 mA per gel at constant current for approximately 75 minutes. Gels were stained in Coomassie Brilliant Blue R-250 (Bio-Rad, Richmond, Calif.) for at least 1 hour and destained. Molecular weight standards were prestained (Mid Range Kit, Diversified Biotech, Newton Center, Mass.) and included the following proteins: Phosphorylase b, glutamate dehydrogenase, ovalbumin, lactate dehydrogenase, carbonic amhydrase, B-lactoglobulin and cytochrome C. The corresponding MWs are: 95,500, 55,000, 43,000, 36,000, 29,000, 18,400, and 12,400, respectively.

When Western analyses were conducted, a duplicate gel was also run. After electrophoresis, one of the gels was equilibrated for 15–20 minutes in anode buffer #1 (0.3M Tris-HCl pH 10.4). An Immobilon-P PVDF (polyvinylidene dichlorine) membrane (Millipore, Bedford, Mass.) was treated with methanol for 2 seconds, and immersed in water for 2 minutes. The membrane was then equilibrated in anode buffer #1 for 3 minutes. A Milliblot-SDE apparatus (Millipore) was utilized to transfer proteins in the gel to the membrane. A drop of anode buffer #1 was placed in the middle of the anode electrode surface. A sheet of Whatman 3 MM filter paper was soaked in anode buffer #1 and smoothly placed on the electrode surface. Another filter paper soaked in anode buffer #2 (25 mM tris pH 10.4) was placed on top of the first one. A sandwich was made by next adding the wetted PVDF membrane, placing the equilibrated gel on top of this and finally adding a sheet of filter paper soaked in cathode buffer (25 mM Tris-HCl, pH 9.4 in 40 mM glycine). Transfer was accomplished in 30 minutes using 250 mA constant current (initial voltage ranged from 8–20 volts).

After blotting, the membrane was rinsed briefly in water and placed in a dish with 20 mL blocking solution (1 percent bovine serum albumin (BSA) (Sigma, St. Louis, Mo.) in Tris-buffered saline (TBS)). TBS was purchased from Pierce Chemical (Rockford, Ill.) as a preweighed powder such that when 500 mL water is added, the mixture gives a 25 mM Tris, 0.15M sodium chloride solution at pH 7.6. The membranes were blocked for a minimum of 1 hour at ambient temperature and then washed 3 times for 5 minutes each using 20 mL 0.5 percent Tween-20 wash solution (TTBS). To prepare the TTBS, 0.5mL of Tween 20 (Sigma) was mixed per liter of TBS. The probe antibody used was 20 mL biotinylated FAID14 solution (10 µg per 20 mL antibody buffer). Antibody buffer was made by adding 1 g BSA per 100 mL of TTBS. After probing for 30–60 minutes at ambient temperature, the membrane was washed 3 times with TTBS, as above.

Next, the membrane was incubated for 30–60 minutes at ambient temperature with 20 mL of a 1:500 dilution in antibody buffer of streptavidin conjugated with alkaline phosphatase (Southern Biotechnology Associates, Birmingham, Ala.). The wash step was again repeated after this, as above. Prior to the color reaction, membranes were washed for 2 minutes in an alkaline carbonate buffer (20 mL). This buffer is 0.1M sodium bicarbonate, 1 mM $MgCl_2 \cdot H_2O$, pH 9.8. To make up the substrate for alkaline phosphatase, nitroblue tetrazolium (NBT) chloride (50 mg, Sigma) was dissolved in 70 percent dimethylformamide. 5-Bromo-4-chloro-3-indoyl phosphate (BCIP) (25 mg, Sigma) was separately dissolved in 100 percent dimethylformamide. 5-Bromo-4-chloro-3-indoyl phosphate (BCIP) 25 mg, Sigma) was separately dissolved in 100 percent dimethylformamide. These solutions are also commercially available as a Western developing agent sold by Promega. For color development, 120 µL of each were added to the alkaline solution above and allowed to react for 15 minutes before they were washed from the developed membranes with water.

Biotinylated FAID14

FAID14 is a murine anti-idiotypic antibody (IgG2a, K isotype) deposited as ATCC No. CRL 10256 directed against CC49. FAID14 was purified using a Nygene Protein A affinity column (Yonkers, N.Y.). The manufacturer's protocol was followed, except that 0.1M sodium citrate, pH 3.0 was used as the elution buffer. Fractions were neutralized to pH ~7 using 1.0M Tris-HCl pH 9.0. The biotinylation reaction was set up as follows. FAID14 (1 mg, 100 µL in water) was mixed with 100 µL of 0.1M $Na_2CO_3$ pH 9.6. Biotinyl-ε-amino-caproic acid N-hydroxy succinimide ester (Biotin-X-NHS) (Calbiochem, LaJolla, Calif.) (2.5 mg) was dissolved in 0.5 mL dimethylsulfoxide. Biotin-X-NHS solution (20 µL) was added to the FAID14 solution and allowed to react at 22° C. for 4 h. Excess biotin and impurities were removed by gel filtration, using a Pharmacia Superose 12 HR10/30 column (Piscataway, N.J.). At a flow rate of 0.8 mL/min, the biotinylated FAID14 emerged with a peak at 16.8 min. The fractions making up this peak were pooled and stored at 4° C. and used to detect the CC49 idiotype as determined by the CC49 $V_L$ and $V_H$ CDRs.

Isoelectric Focusing (IEF)

Isoelectric points (pI's) were predicted using a computer program called PROTEIN-TITRATE, available through DNASTAR (Madison, Wis.). Based on amino acid composition with an input sequence, a MW value is given, in addition to the pI. Since Cys residues contribute to the charge, the count was adjusted to 0 for Cys, since they are all involved in disulfide bonds.

Experimentally, pI's were determined using Isogel agarose IEF plates, pH range 3–10 (FMC Bioproducts, Rockland, Me.). A Biorad Bio-phoresis horizontal electrophoresis cell was used to run the IEF, following the directions of both manufacturers. The electrophoresis conditions were: 500 volts (limiting), at 20 mA current and 10 W of constant power. Focusing was complete in 90 min. IEF standards were purchased from Biorad; the kit included phycocyanin, β-lactoglobulin B, bovine carbonic anhydrase, human carbonic anhydrase, equine myoglobin, human hemoglobins A and C, 3 lentil lectins and cytochrome C, with pI values of 4.65, 5.10, 6.00, 6.50, 7.00, 7.10 and 7.50, 7.80, 8.00, and 8.20 and 9.60 respectively. Gels were stained and destained according to the directions provided by FMC.

Quantitation of CC49 Antibody Species

All purified CC49 antibodies including the IgG, scFv2 species and the monomeric scFv were quantitated by measuring the absorbance of protein dilutions at 280 mm using matching 1.0 cm pathlength quartz cuvettes (Hellma) and a Perkin-Elmer UV/VIS Spectrophotometer, Model 552A. Molar absorptivities ($E_m$) were determined for each antibody by using the following formula:

$$E_m=(\text{number Trp})\times 5{,}500+(\text{number Tyr})\times 1{,}340+(\text{number Cys}/2)\times 150+(\text{number Phe})\times 10$$

The values are based on information given by D. B. Wetlaufer, *Advances in Protein Chemistry*, 17, 375–378).

High Performance Liquid Chromatography

All high performance liquid chromatography (HPLC) was performed for CC49 scFv2 purification using an LKB HPLC system with titanium or teflon using throughout. The system consists of the Model 2150 HPLC pump, model 2152 controller, UV CORD SII model 2233 detection system set at an absorbance of 276 nm and the model 2211 SuperRac fraction collector.

PCR Generation of Subunits

All polymerase chain reactions (PCR) were performed with a reaction mixture consisting of: 150 picograms (pg) plasmid target (pSCFVUHM); 100 pmoles primers; 1 μL Perkin-Elmer-Cetus (PEC, Norwalk, Conn.) Ampli-Taq polymerase; 16 μL of 10 mM dNTPs and 10 μL of 10× buffer both supplied in the PEC kit; and sufficient water to bring the volume to total volume to 100 μL. The PCR reactions were carried out essentially as described by the manufacturer. Reactions were done in a PEC 9600 thermocycler with 30 cycles of: denaturation of the DNA at 94° C. for 20 to 45 sec, annealing from between 52° to 60° C. for 0.5 to 1.5 min., and elongation at 72° C. for 0.5 to 2.0 min. Oligonucleotide primers were synthesized on an Applied Biosystems (Foster City, Calif.) 380A or 391 DNA synthesizer and purified as above.

Ligations

Ligation reactions using 100 ng of vector DNA and a corresponding 1:1 stoichiometric equivalent of insert DNA were performed using a Stratagene (La Jolla, Calif.) T4 DNA ligase kit following the manufacturer's directions. Ligation reactions (20 μL total volume) were initially incubated at 18° C. and allowed to cool gradually overnight to 4° C.

Transformations

Transformations were performed utilizing 100 μL of Stratagene *E. coli* AG1 competent cells (Stratagene, La Jolla, Calif.) according to the directions provided by the manufacturer. DNA from the ligation reactions (1–5 μL) were used. After the transformation step, cells were allowed to recover for 1 hr in Luria broth (LB) at 37° C. with continuous mixing and subsequently plated onto either 20 μg/mL chloramphenicol containing (CAM 20) Luria agar for pSCFVUHM, p49LHLH or p49LHHL or 100 μg/mL ampicillin (AMP 100) Luria agar plates (LB-AMP 100) for clones containing the plasmid pSL301 or subsequent constructions derived from pSL301.

Screening of *E. coli* Clones

Bacterial plasmids were isolated from LB broth culture containing the appropriate drug to maintain selection pressure using Promega (Madison, Wis.) Magic mini-prep plasmid preparation kits. The kit was used per the manufacturer's specifications.

Plasmid Constructions

Two plasmids, designated p49LHLH and p49LHHL, were constructed to produce multivalent single chain antibodies. The host cell containing p49LHLH produced a polypeptide which can be designated by $V_L$-L-$V_H$-L-$V_L$-L-$V_H$ where $V_L$ and $V_H$ are the light and heavy cahin variable regions of CC49 antibody and linker (L) is a 25 amino acid linker having the sequence (SEQ ID NO: 5).
Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu.

The host cell containing p49LHHL produced a polypeptide which can be designated by $V_L$-L-$V_H$-L-$V_H$-L-$V_L$ where $V_L$ and $V_H$ are the light and heavy chain variable domains of the CC49 antibody and L is a peptide linker having the amino acid sequence indicated above.

The nucleotide sequence (SEQ ID NO: 6) and amino acid sequence (SEQ ID NO: 7) of the CC49 $V_L$-L-$V_H$-L-$V_L$-L-$V_H$ (p49LHLH) are given in FIG. 6. The nucleotide sequence (SEQ ID NO: 8) and amino acid sequence (SEQ ID NO: 9) of the CC49 $V_L$-L-$V_H$-L-$V_H$-L-$V_L$ (p49LHHL) are given in FIG. 7.

Construction of pSL301 HT

The construction of pSL301 HT is illustrated in FIG. 8. The *Bacillus lichiformis* penicillinase P (penP) terminator sequence was removed from the plasmid designated pSCFV UHM by a 45 minute digest with Nhe I. and BamH I, excised from a 4.5 percent polyacrylamide gel after electrophoresis, electroeluted, ethanol precipitated and ligated into the same sites in the similarly prepared vector: pSL301 (Invitrogen, San Diego, Calif.). A procedure for preparing pSCFV UHM is given is U.S. patent application Ser. No. 07/935,695 filed Aug. 21, 1992, the disclosure of which is hereby incorporated by reference. In general, pSCFV UHM contains a nucleotide sequence for a penP promoter; a unique Nco I restriction site; CC49 $V_L$ region; HindIII restriction site; a 25 amino acid linker; a unique a Xho I restriction site; CC49 $V_H$ region; Nhe I restriction site; penP terminator; and BamH I restriction site (see, FIG. 8). The penP promoter and terminator are described in Mezes, et al. (1983), *J. Biol. Chem.*, 253, 11211–11218 (1983).

An aliquot of the ligation reaction (3 μL) was used to transform competent *E. coli* AG1 cells which were plated on LB-AMP100 agar plates and grown overnight. Potential clones containing the penP terminator insert were screened using a Pharmacia (Gaithersburg, Md.) T7 Quickprime $^{32}$P DNA labeling kit in conjunction with the microwave colony lysis procedure outlined in Buluwela et al., *Nucleic Acid Research*, 17, 452 (1989). The probe, which was the penP-Nhe I-BamH I terminator fragment itself was prepared and used according to the directions supplied with the Quickprime kit. A clone which was probe positive and which contained the 207 base pair inserts from a BamH I and Nhe I digest (base pairs (bp) 1958 to 2165, FIG. 6) was designated pSL301 T and chosen to construct pSL301 HT which would contain the nucleotide sequence for CC49 $V_H$. The reason the Nhe I-BamH I penP terminator was placed into pSL301 was to eliminate the Eco47 III restriction endonuclease site present in the polylinker region between its Nhe I and BamH I sites. This was designed to accomodate the subsequent build-up of the $V_L$ and $V_H$ domains where the Eco47 III site needed to be unique for the placement of each successive V domain into the construction. As each V domain was added at the Eco47 III-Nhe I sites, the Eco47 III was destroyed in each case to make the next Eco47 III site coming in on the insert unique.

The $V_H$ sequence was made by PCR with oligos 5' SCP1 and 3'oligo SCP5 using pSCFV UHM as the target for PCR amplification. The DNA sequence for SCP1 (SEQ ID NO: 10) and SCP5 (SEQ ID NO: 11) are as follows:
SCP1: 5'-TAAA <u>CTC GAG</u> GTT CAG TTG CAG CAG -3'
SCP5: 5'-TAAA <u>GCT AGC</u> ACCA <u>AGC GCT</u> TAG TGA GGA GAC GGT GAC TGA GGT-3'
The underlined portion indcates the endonuclease restriction sites.

The amplified $V_H$ DNA was purified from a 4 percent PAG, electroeluted ethanol precipitated and dissolved in 20 μL water. The $V_H$ sequence was digested with Xho I and Nhe I restriction enzymes and used as the insert with the pSL301 T vector which had been digested with the same restriction enzymes and subsequently purified. A standard ligation reaction was done and an aliquot (4 μL) used to transform competent E. coli AG1 cells. The transformed cells were plated onto LB AMP100 agar plates. Candidate clones were picked from a Nhe I and Xho I digest screen that revealed that the CC49$V_H$ insert had been obtained.

DNA sequencing was performed to verify the sequence of the CC49$V_H$ with United States Biochemical (USB) (Cleveland, Ohio) Sequence kit and sequencing primers pSL301SEQB (a 21 bp sequencing primer which annealed in the pSL301 vector 57 bp upstream from the Xho I site) and CC49VHP, revealed clones with the correct CC49$V_H$ sequence in pSL301HT. This plasmid was used as the starting point in the construction of both pSL301-HHLT and pSL301-HLHT. The sequencing oligos used are shown here.

The nucleotide sequence of pSL301SEQ B (SEQ ID NO: 12) and CC49$V_H$ (SEQ ID No: 13) are as follows:
pSL301SEQB: 5'-TCG TCC GAT TAG GCA AGC TTA-3'
CC49VHP: 5'-GAT GAT TTT AAA TAC AAT GAG-3'

Example 1 p49LHHL Construction

Using pSL301 HT (5 μg) as the starting material, it was digested with Eco47 III and Nhe I and the larger vector fragment was purified. A CC49$V_H$ insert fragment was generated by PCR using SCP6C as the 5' oligo and SCP5 as the 3' oligo. The nucleotide sequence (SEQ ID NO: 14) of SCP6B is as follows:
SCP6B: 5'-TAAA <u>TGC GCA</u> GAT GAC GCA AAG AAA GAC GCA GCT AAA AAA GAC GAT GCC AAA AAG GAT GAC GCC AAG AAA GAT CTT GAG GTT CAG TTG CAG CAG TCT-G'
The oligo SCP6B also contains part of the coding region for the linker (bp 8–76 of SEQ ID NO: 14). The portion of the oligo designed to anneal with the CC49VH target in pSCFV UHM is from bp77–90 in SEQ ID NO: 14.

The underlined sequence corresponds to the Fsp I site. The resulting PCR insert was purified, digested with Fsp I and Nhe I and used in a ligation reaction with the pSL301 HT Eco47 III-Nhe I vector (FIG. 7). Competent E. coli AG1 cells were used for the transformation of this ligation reaction (3 μL) and were plated on LB-AMP100 agar plates. Two clones having the correct size Xho I-Nhe I insert representative of the pSL301 HHT product were sequenced with the oligo SQP1 and a single clone with the correct sequence (nucleotides 1124–1543 of FIG. 7) was chosen for further construction. The nucleotide sequence of SQPL (SEQ ID NO: 15) is as follows:
SQP1: 5'-TG ACT TTA TGT AAG ATG ATG T-3'

The final linker-$V_L$ subunit (bp 1544–1963, FIG. 7) was generated using the 5'oligo, SCP7b and the 3' oligo, SCP8a, using pSCFV UHM as the target for the PCR. The nucleotide sequence of SCP7b (SEQ ID NO: 16 is as follows:
SCP7b: 5'-TAAA <u>TGC GCA</u> GAT GAC GCA AAG AAA GAC GCA GCT AAA AAA GAC GAT GCC AAA AAG GAT GAC GCC AAG AAA GAT CTT GAC ATT GTG ATG TCA CAG TCT CC The underlined nucleotides correspond to an Fsp I site. The nucleotide sequence of SCP8a (SEQ ID NO: 17) is as follows:
SCP8a: 5'-TAAA <u>GCT AGC</u> TTT TTA <u>CTT AAG</u> CAC CAG CTT GGT CCC-3'

The first set of underlined nucleotides correspond to an Nhe I site, while the other corresponds to an Afl II site. Nucleotides 8–76 of SCP70 code for the linker (nucleotides 1544–1612 of FIG. 7) while nucleotides 77–99 which anneal to the $V_L$ correspond to 1613–1635 of FIG. 7. The primer SCP8a has a short tail at its 5' end, a Nhe I restriction site, a stop codon, an Afl II restriction site and the last 21 bases of the $V_L$. After Fsp I and Nhe I digestion, this resulting 420 bp insert was purified and ligated into the Nhe I and Eco47 III sites of the purified pSL301HHT vector, candidate clones were screened with Nhe I and Xho I, the correct size insert verified and sequenced with 49LFR2(-) and SQP1 to confirm the newly inserted sequence in pSL301HHLT. The nucleotide sequence (SEQ ID NO: 18) is as follows:
49LFR2(-): 5'-CTG CTG GTA CCA GGC CAA G-3'

The plasmid pSL301HHLT was digested with Xho I and Nhe I, purified, and the resulting 1179 bp $V_H$-linker-$V_H$-linker-$V_L$ segment ligated into pSCFV UHM, which had been cut with the same restriction enzymes and the larger vector fragment purified, to form p49LHHL. The ligation reaction (4 μL aliquot) was used to transform competent E. coli AG1 cells (Stratagene) and plated onto LBCAM20 agar plates. A single clone which had a plasmid with the correct restriction enzyme map was selected to contain p49LHHL. The p49LHHL contains a penP promotor and a nucleotide sequence for the CC49 multivalent single chain antibody scFv2: $V_L$-L-$V_H$-L-$V_H$-L-$V_L$ or CC49 scFv2 (LHHL).

Example 2 p49LHLH Construction

Figure 10:
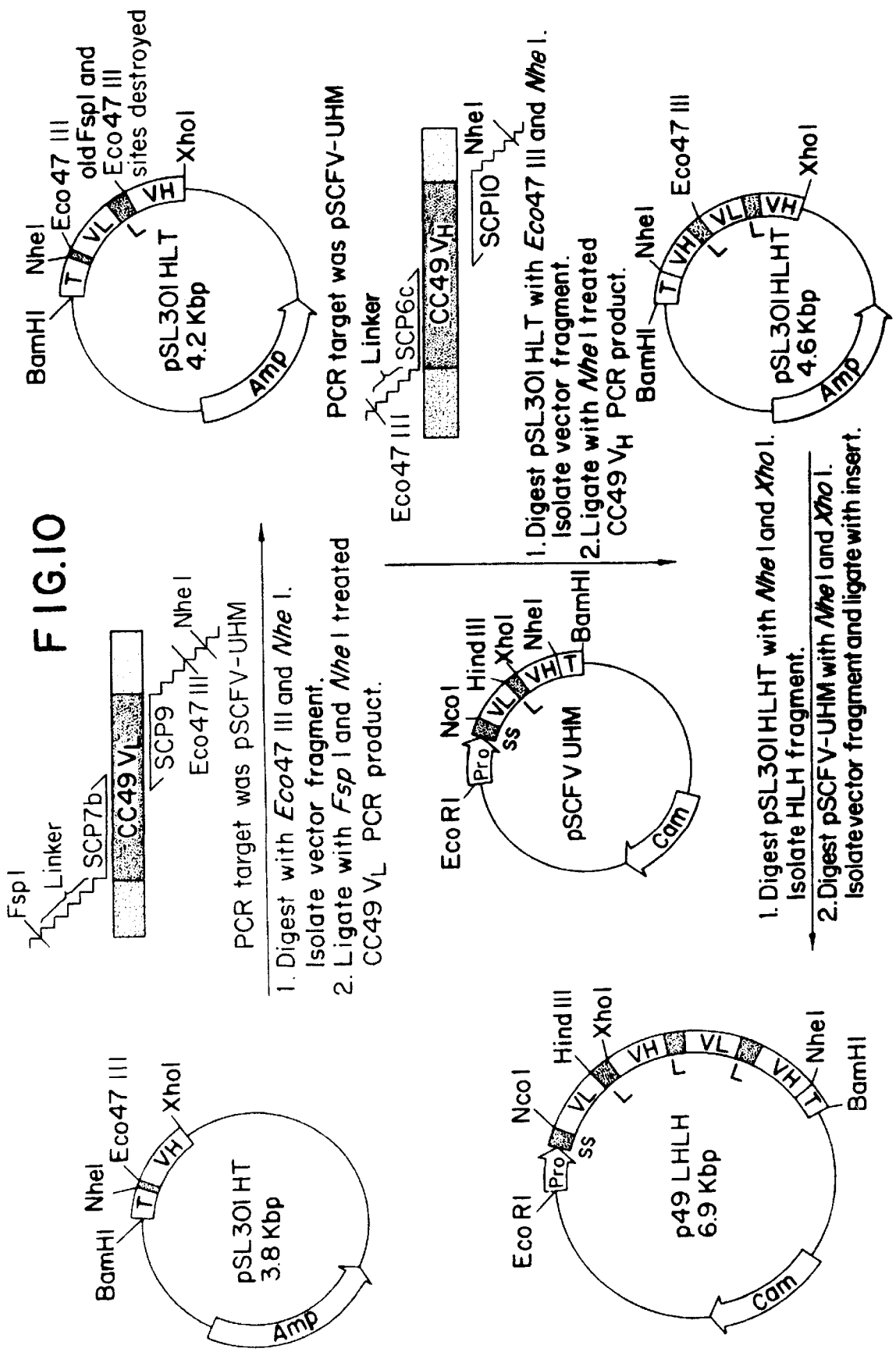
FIG. 10 illustrates construction of plasmid p49LHLH.

The construction of p49LHLH is schematically represented in FIG. 10. A linker-$V_L$ subunit was generated with the 5' oligo SCP7b and the 3'oligo SCP9 (SEQ ID NO: 19).
SCP9: 5'-TAA <u>AGC TAG CAC CAA GCG CTT</u> AGT TTC AGC ACC AGC TTG GTC CCA G-3'

The SCP7b oligo (nucleotides 8–76) codes for the linker in FIG. 6 (corresponding to nucleotides 1124–1192) and annealed to the pSCFV UHM target for the PCR (nucleotides 77–99) corresponding to nucleotides 1193–1215 of the $V_L$ in FIG. 6.

SCP9 has a Nhe I site (first underlined nucleotides) and an Eco47 III site (second underlined nucleotides) which are restriction sites needed for making the pSL301HLT ready to accept the next V domain. Nucleotides 18–23 of SCP9 correspond to nucleotides 1532–1537 of FIG. 6 (coding for the first 2 amino acids of the linker), while nucleotides 24–46 correspond to nucleotides 1508–1531 of FIG. 6 which was also the annealing. region for SCP9 in the PCR. The plasmid pSL301 HT was digested with Eco47 III and Nhe I and the larger vector fragment was purified for ligation with the linker-CC49$V_L$ DNA insert fragment from the PCR which had been treated with Fsp I and Nhe I and purified. The ligation mixture (3 μL) was used to transform E. coli AG1 competent cells and one colony having the correct Xho I-Nhe I size fragment was sequenced using the oligo PENPTSEQ2. The nucleotide sequence (SEQ. ID NO. 20) is as follows:

5'-TTG ATC ACC AAG TGA CTT TAT G-3'

The sequencing results indicated that there had been a PCR error and deletion in the resulting pSL301HT clone. A five base deletion, corresponding to nucleotides 1533–1537 as seen in FIG. 6 had been obtained and nucleotide 1531 which should have been a T was actually a G, as determined from the DNA sequence data. The resulting sequence was 5' . . . G AAGC GCT T . . . etc.

where the underlined sequence fortuitously formed an Eco47 III site. The AGCGCT sequence in FIG. 6, would correspond to nucleotides 1530, 1531, 1532, 1538, 1539 and 1540. This error was corrected in the next step, generating pSL301 HLHT, by incorporating the 5 base deletion at the end of oligo SCP6C (SEQ ID NO: 21).

SCP6C: 5'-TAAGCGCTGATGATGCTAAGAAGGACGCCGCAAAAAAGGACGACGCAAAAAAAGATGATG-CAAAAAAGGATCTGGAGGTTCAGTTGCAGCAGTCTGAC-3'

The underlined sequence in SCP6c corresponds to an Eco47 III site. SCP6C was used as the 5' oligo, with SCP10 as the 3' oligo in a PCR to generate a linker CC49 $V_L$ segment. The nucleotide sequence (SEQ ID NO: 22) is as follows:

SCP10: 5'TTG TGC TAG CTT TTT ATG AGG AGA CGG TGA CTG AGG TT-3'

The underlined sequence in SCP10 corresponds to the Nhe I site found at nucleotides 1958–1963 in FIG. 6. The PCR insert was digested this time only with Nhe I and purified. The vector (pSL301 HLT) was digested at the Eco47 III site (that had been formed) and Nhe I and purified. The insert and vector were ligated and an aliquot (3 µL) used to transform competent E. coli AG1 cells. This was plated on LB-AMP100 plates and candidate clones screened with Xho I and Nhe I. Three clones having the correct size DNA were obtained. Two of these clones were sequenced using the oligo 49VLCDR3(+) and SQP1. The nucleotide sequence (SEQ ID NO: 23 of 49VLCDR3(+) is as follows:

49VLCDR3(+):
5'-CAG CAG TAT TAT AGC TAT-3'

One clone, with the correct sequence was obtained and the sequence from nucleotides 1533 to 1963 in FIG. 6 were verified, giving a correct pSL301 HLHL clone.

To generate the final plasmid, p49LHLH for expression in E. coli, pSL301 HLHT (5 µg) was digested with Nhe I and Xho I, and the smaller insert fragment containing the $V_H$-L-$V_L$-$V_H$ sequence purified. It was ligated with the larger purified vector fragment from a digest of pSCFV UHM (5 µg) with Xho I and Nhe I. An aliquot of the ligation mix (4 µL) was used to transform competent E. coli AG1 cells. The transformation mix was plated on LB-CAM20 plates, and a representative clone for p49 LHLH was selected on the basis of a correct restriction enzyme map (see FIG. 10) and biological activity toward TAG-72.

Example 3

Purification of CC49 scFv2 LHLH and LHHL Covalently Linked Dimers

For the purification of the CC49 covalently linked single chain dimers, (scFv2), E. coli periplasmic fractions were prepared from 1.0 L overnight cultures of both p49LHLH and p49LHHL. Briefly, the culture was divided into 4×250 mL portions and centrifuged at 5,000 rpm for 10 minutes in a Sorvall GS-3 rotor. The pelleted cells were washed and resuspended in 100 mL each of 10 mM Tris-HCl pH 7.3 containing 30 mM NaCl. The cells were again pelleted and washed with a total of 100 mL 30 mM Tris-HCl pH 7.3 and pooled into one tube. To this, 100 mL of 30 mM Tris-HCl pH 7.3 containg 40 percent w/v sucrose and 2.0 mL of 10 mM EDTA pH 7.5 was added. The mixture was kept at room temperature, with occasional shaking, for 10 minutes. The hypertonic cells were then pelleted as before. In the next step, the shock, the pellet was quickly suspended in 20 mL ice cold 0.5 mM $MgCl_2$ and kept on ice for 10 minutes, with occasional shaking. The cells were pelleted as before and the supernatant containing the E. coli periplasmic fraction was clarified further by filtration through a 0.2 µm Nalge (Rochester, N.Y.) filter apparatus and concentrated in Amicon (Danvers, Mass.) Centriprep 30 and Centricon 30 devices to a volume of less than 1.0 mL.

The concentrated periplasmic shockates from either the p49LHLH or p49LHHL clones were injected onto a Pharmacia (Piscataway, N.J.) Superdex 75 HR 10/30 HPLC column that had been equilibrated with PBS. At a flow rate of 0.5 mL/minute, the product of interest, as determined by competition ELISA, had emerged between 21 through 24 minutes. The active fractions were pooled, concentrated as before and dialyzed overnight using a system 500 Microdialyzer Unit (Pierce Chemical) against 20 mM Tris-HCl pH 7.6 with 3–4 changes of buffer and using an 8,000 MW cut-off membrane. The sample was injected on a Pharmacia Mono Q HR 5/5 anion exchange HPLC column. A gradient program using 20 mM Tris-HCl pH 7.6 as buffer A and the same solution plus 0.5M NaCl as buffer B was employed at a flow rate of 1.5 mL/min. The products of interest in each case, as determined by competition ELISA, emerged from the column between 3 and 4 minutes. Analysis of the fractions at this point on duplicate SDS-PAGE gels, one stained with Coomassie Brilliant Blue R-250 and the other transferred for Western analysis (using biotinylated FAID 14 as the probe antibody) revealed a single band at the calculated molecular weight for the scFv2 (LHLH or LHHL) species at 58,239 daltons. The active fractions were in each case concentrated, dialysed against 50 mM MES pH 5.8 overnight and injected on a Pharmacia Mono S HR 5/5 cation exchange column. The two fractions of interest from this purification step, as determined by SDS-PAGE and ELISA, fractions 5 and 6, eluted just before the start of the gradient, so they had not actually bound to the column. Fractions 5 and 6 were consequently pooled for future purification.

A Mono Q column was again run on the active Mono S fractions but the buffer used was 20 mM Tris-HCl, pH 8.0 and the flow rate was decreased to 0.8 mL/minute. The products emerged without binding, but the impurity left over from the Mono S was slightly more held up, so that separation did occur between 5 and 6 minutes. After this run, the products were homogeneous and were saved for further characterization.

Isoelectric Focusing

The isoelectric points (pI) of the constructs was predicted using the DNASTAR (Madison, Wis.) computer program Protein-titrate. Based on amino acid composition, a MW and pI value was calculated.

Experimentally, pIs were determined using FMC Bioproducts (Rockland, Me.) Isogel IEF plates, pH range 3–10. A Biorad (Richmond, Calif.) electrophoresis unit was used to run the IEF, following the directions of both manufacturers. The electrophoresis conditions were as follows: 500 V (limiting) at 20 mA and at 10 W of constant power. Focusing was complete in 90 minutes. Biorad IEF standards included phycocyanin, beta lactoglobulin B, bovine carbonic anhydrase, human carbonic anhydrase, equine myoglobulin, human hemeglobins A and C, 3 lentil lectin, and cytochrome C with pI value of 4.65, 5.10, 6.00, 6,50, 7.00, 7.50, 7.8, 8.00, 8.20 and 9.6 respectively. Gels were stained and destained according to directions provided by FMC. The DNASTAR program predicted values of 8.1 for the pI for both scFv2 species. A single, homogeneous band for the pure products was observed on the gel at pI values for both at 6.9.

Purified CC49 antibodies such as the IgG, scFv2 (LHLH and LHHL) were quantitated by measuring the absorbance spectrophotometrically at 280 nm. Molar absorbtivity values, $\epsilon_M$, were determined for each using the formula cited above by Wetlaufer.

Based on the amino acid composition, the $E^{0.1\%}$ (280 nanometers) values for CC49 IgG, CC49 scFv2 LHLH, CC49 scFv2 LHHL and CC49 scFv were 1.49, 1.65, 1.65 and 1.71 respectively.

Example 4

Relative activities of the CC49 scFv2 species LHLH and LHHL, were compared with the IgG and a monomer scFv form with a FLAG peptide at the COOH terminus.

Percent competition was determined from the ELISA data by the following equation:

$$\frac{\text{Zero competition} - \text{sample reading} (OD405-450 \text{ nm})}{\text{zero competition} - 100 \text{ percent competition}} \times 100$$

Figure 11:
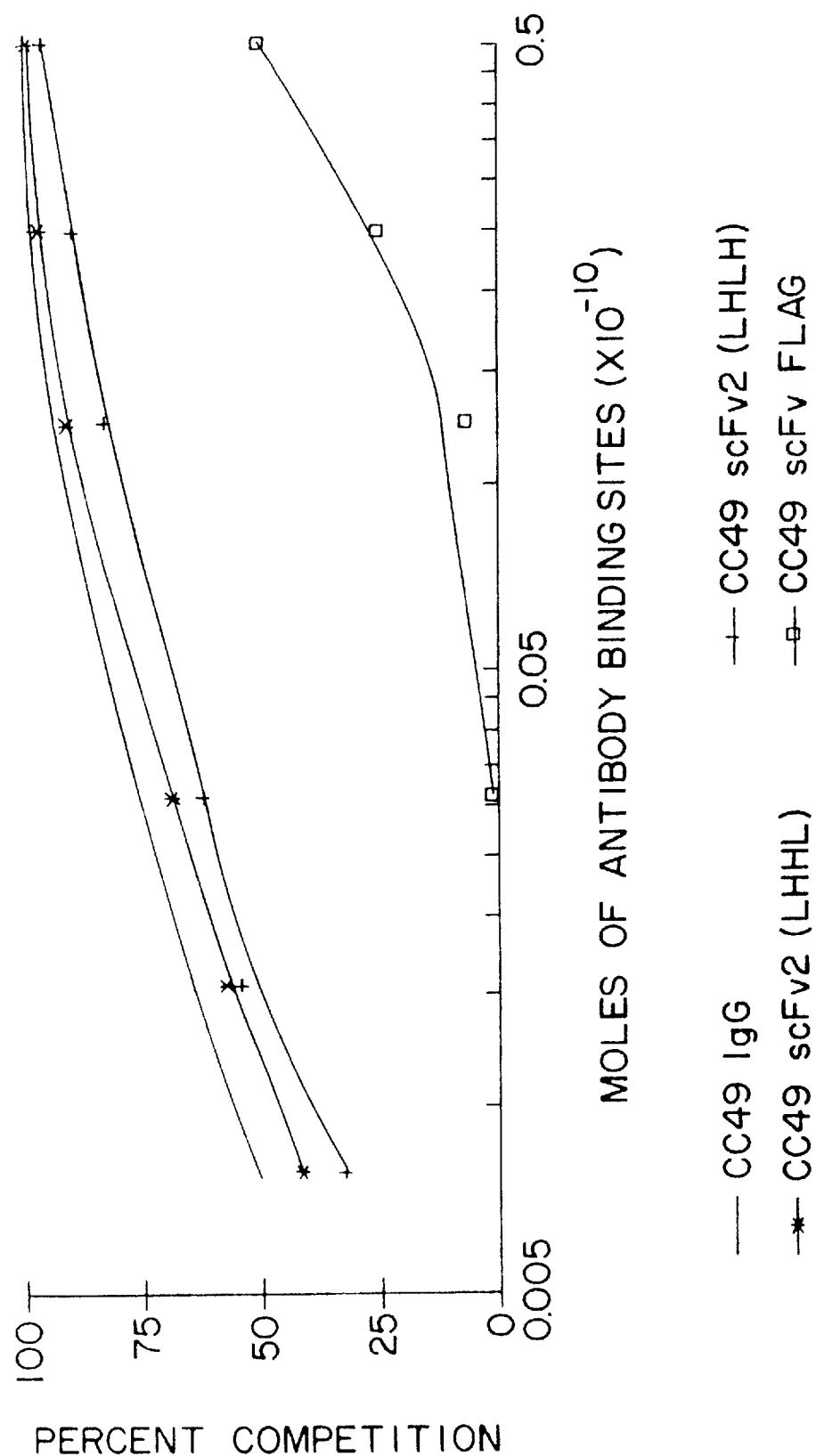
FIG. 11 illustrates the results of a competition assay using CC49 IgG, CC49 scFv2, and CC49 scFv using biotinylated CC49 IgG as competitor.

The "zero competition" value was determined by mixing (1:1) one percent BSA with the biotinylated CC49 (3×10−14 moles) while the 100 percent competition value was based on a 5 µg/mL sample of CC49 IgG mixed with the biotinylated CC49 IgG. The data are presented in FIG. 11. Absorbance values for the samples were measured at 405 nm–450 nm. The average of triplicate readings was used. Initially samples (25 µL) were applied to the TAG-72 coated microliter plates at 1.0×10−10 moles of binding sites/mL. Biotinylated CC49 (4 µg/pL diluted 1:20,000—used 25 µL) diluted the samples by a factor of 2. Serial dilutions (1:2) were performed. Both forms of the scFv2 are approximately equivalent to the IgG (see FIG. 11). In a separate experiment, a CC49 scFv monomer was compared to a Fab fragment, both of which are monovalent and these were also shown to be equivalent in their binding affinity for TAG-72. These results indicate that both forms of the covalently linked dimers have 2 fully functional antigen binding sites. This is the same increase in avidity as observed with the whole IgG, relative to a monomeric species.

These data also indicate that the scFv2 molecules, like their CC49 IgG parent are candidates for immunotherapeutic applications, but with the benefit of increased capillary permeability and more rapid biodistribution pharmacokinetics. The advantage should allow multiple injections of compounds of the present invention and give higher tumor-:tissue ratios in immunotherapeutic treatment regimens for cancer treatment, relative to the existing IgG molecules.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A DNA sequence which codes for a multivalent single chain antibody, the multivalent single chain antibody comprising two or more single chain antibodies and at least one first peptide linker, each single chain antibody having affinity for TAG-72, each single chain antibody being covalently linked by at least one of said first peptide linkers to at least one other single chain antibody and each single chain antibody comprising:

(a) a first polypeptide comprising a light chain variable domain encoded by a base sequence whose expression product is substantially homologous to that having the amino acid sequence (SEQ ID NO: 2) of Asp Ile Val Met Ser Gln Ser Pro Ser Ser Leu Pro
Val Ser Val Gly Glu Lys Val Thr Leu Ser Cys Lys
Ser Ser Gln Ser Leu Leu Tyr Ser Gly Asn Gln Lys
Asn Tyr Leu Ala Trp Tyr Gln Gln Lys Pro Gly Gln
Ser Pro Lys Leu Leu Ile Tyr Trp Ala Ser Ala Arg
Glu Ser Gly Val Pro Asp Arg Phe Thr Gly Ser Gly
Ser Gly Thr Asp Phe Thr Leu Ser Ile Ser Ser Val
Lys Thr Glu Asp Leu Ala Val Tyr Tyr Cys Gln Gln
Tyr Tyr Ser Tyr Pro Leu Thr Phe Gly Ala Gly Thr
Lys Leu Val Leu Lys and whose expression product retains the characteristic of functional binding to TAG-72;

(b) a second polypeptide comprising a heavy chain variable domain encoded by a base sequence whose expression product is substantially homologous to that having the amino acid sequence (SEQ ID NO: 4) of Glu Val Gln Leu Gln Gln Ser Asp Ala Glu Leu Val
Lys Pro Gly Ala Ser Val Lys Ile Ser Cys Lys Ala
Ser Gly Tyr Thr Phe Thr Asp His Ala Ile His Trp
Val Lys Gln Asn Pro Glu Gln Gly Leu Glu Trp Ile
Gly Tyr Phe Ser Pro Gly Asn Asp Asp Phe Lys Tyr
Asn Glu Arg Phe Lys Gly Lys Ala Thr Leu Thr Ala
Asp Lys Ser Ser Ser Thr Ala Tyr Val Gln Leu Asn
Ser Leu Thr Ser Glu Asp Ser Ala Val Tyr Phe Cys
Thr Arg Ser Leu Asn Met Ala Tyr Trp Gly Gln Gly
Thr Ser Val Thr Val Ser Ser and whose expression product retains the characteristic of functional binding to TAG-72; and (c) a second peptide linker linking the first and second polypeptides into a functional binding moiety;

wherein said first peptide linker comprises a 15–25 amino acid segment of the amino acid sequence (SEQ ID NO: 5), Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu, and said multivalent single chain antibody has an affinity of at least 60% of that of a native anti-TAG-72 antibody, as measured by a competitive binding assay.

2. A DNA sequence which codes for a multivalent single chain antibody, the multivalent single chain antibody comprising two or more single chain antibodies and at least one first peptide linker, each single chain antibody (a) having affinity for TAG-72;

(b) being covalently linked, by at least one of said first peptide linkers, to at least one other single chain antibody; and (c) comprising a first polypeptide capable of binding TAG-72, covalently linked by a second peptide linker to a second polypeptide capable of binding TAG-72;

wherein:

(1) the first peptide linker comprises a 15–25 amino acid segment of the amino acid sequence (SEQ ID NO: 5), Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu; and (2) the multivalent single chain antibody has an affinity of at least 60% of that of a native anti-TAG-72 antibody, as measured by a competitive binding assay.

3. The DNA sequence of claim 2 wherein the sequence coding for the first polypeptide comprises a base sequence whose expression product has the amino acid sequence (SEQ ID NO: 2) of

| Asp | Ile | Val | Met | Ser | Gln | Ser | Pro | Ser | Ser | Leu | Pro |
|---|---|---|---|---|---|---|---|---|---|---|---|
| Val | Ser | Val | Gly | Glu | Lys | Val | Thr | Leu | Ser | Cys | Lys |
| Ser | Ser | Gln | Ser | Leu | Leu | Tyr | Ser | Gly | Asn | Gln | Lys |
| Asn | Tyr | Leu | Ala | Trp | Tyr | Gln | Gln | Lys | Pro | Gly | Gln |
| Ser | Pro | Lys | Leu | Leu | Ile | Tyr | Trp | Ala | Ser | Ala | Arg |
| Glu | Ser | Gly | Val | Pro | Asp | Arg | Phe | Thr | Gly | Ser | Gly |
| Ser | Gly | Thr | Asp | Phe | Thr | Leu | Ser | Ile | Ser | Ser | Val |
| Lys | Thr | Glu | Asp | Leu | Ala | Val | Tyr | Tyr | Cys | Gln | Gln |
| Tyr | Tyr | Ser | Tyr | Pro | Leu | Thr | Phe | Gly | Ala | Gly | Thr |
| Lys | Leu | Val | Leu | Lys | | | | | | | | and the sequence coding for the second polypeptide comprises a base sequence whose expression product has the amino acid sequence (SEQ ID NO: 4) of

| Glu | Val | Gln | Leu | Gln | Gln | Ser | Asp | Ala | Glu | Leu | Val |
|---|---|---|---|---|---|---|---|---|---|---|---|
| Lys | Pro | Gly | Ala | Ser | Val | Lys | Ile | Ser | Cys | Lys | Ala |
| Ser | Gly | Tyr | Thr | Phe | Thr | Asp | His | Ala | Ile | His | Trp |
| Val | Lys | Gln | Asn | Pro | Glu | Gln | Gly | Leu | Glu | Trp | Ile |
| Gly | Tyr | Phe | Ser | Pro | Gly | Asn | Asp | Asp | Phe | Lys | Tyr |
| Asn | Glu | Arg | Phe | Lys | Gly | Lys | Ala | Thr | Leu | Thr | Ala |
| Asp | Lys | Ser | Ser | Ser | Thr | Ala | Tyr | Val | Gln | Leu | Asn |
| Ser | Leu | Thr | Ser | Glu | Asp | Ser | Ala | Val | Tyr | Phe | Cys |
| Thr | Arg | Ser | Leu | Asn | Met | Ala | Tyr | Trp | Gly | Gln | Gly |
| Thr | Ser | Val | Thr | Val | Ser | Ser. | | | | | |

4. The DNA sequence of claim 3 wherein the sequence coding for the first polypeptide comprises a base sequence (SEQ ID NO: 1) of

```
GAC ATT GTG ATG TCA CAG TCT CCA TCC TCC CTA CCT
GTG TCA GTT GGC GAG AAG GTT ACT TTG AGC TGC AAG
TCC AGT CAG AGC CTT TTA TAT AGT GGT AAT CAA AAG
AAC TAC TTG GCC TGG TAC CAG CAG AAA CCA GGG CAG
TCT CCT AAA CTG CTG ATT TAC TGG GCA TCC GCT AGG
GAA TCT GGG GTC CCT GAT CGC TTC ACA GGC AGT GGA
TCT GGG ACA GAT TTC ACT CTC TCC ATC AGC AGT GTG
AAG ACT GAA GAC CTG GCA GTT TAT TAC TGT CAG CAG
TAT TAT AGC TAT CCC CTC ACG TTC GGT GCT GGG ACC
AAG CTG GTG CTG AAG
``` and the sequence coding for the second polypeptide comprises a base sequence (SEQ ID NO: 3) of

```
GAG GTT CAG TTG CAG CAG TCT GAC GCT GAG TTG GTG
AAA CCT GGG GCT TCA GTG AAG ATT TCC TGC AAG GCT
TCT GGC TAC ACC TTC ACT GAC CAT GCA ATT CAC TGG
GTG AAA CAG AAC CCT GAA CAG GGC CTG GAA TGG ATT
GGA TAT TTT TCT CCC GGA AAT GAT GAT TTT AAA TAC
AAT GAG AGG TTC AAG GGC AAG GCC ACA CTG ACT GCA
GAC AAA TCC TCC AGC ACT GCC TAC GTG CAG CTC AAC
AGC CTG ACA TCT GAG GAT TCT GCA GTG TAT TTC TGT
ACA AGA TCC CTG AAT ATG GCC TAC TGG GGT CAA GGA
ACC TCA GTC ACC GTC TCC TCA.
```

5. The DNA sequence of claim 2 wherein said multivalent single chain antibody comprises only two of said single chain antibodies covalently linked together by one said first peptide linker.

6. The DNA sequence of claim 2 wherein said DNA sequence is a contiguous sequence.

7. The DNA sequence of claim 2 wherein said DNA sequence comprises at least two exons.

8. The DNA sequence of claim 4 wherein said multivalent single chain antibody comprises only two of said single chain antibodies covalently linked together by one said first peptide linker.

9. The DNA sequence of claim 3 wherein said first and second peptide linkers are about 10 to about 50 amino acids in length.

10. The DNA sequence of claim 9 wherein said linkers are about 12 to about 30 amino acids in length.

11. The DNA sequence of claim 10 wherein said linkers are about 25 amino acids in length.

12. The DNA sequence of claim 11 wherein said linkers comprise the 25 amino acid sequence (SEQ ID NO: 5) of Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu.

13. The DNA sequence of claim 4 wherein said DNA sequence is a contiguous sequence.

14. The DNA sequence of claim 4 wherein said DNA sequence comprises at least two exons.

15. The DNA sequence of claim 2 wherein said second peptide linker comprises a 15–25 amino acid segment of the amino acid sequence (SEQ ID NO: 5), Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu.

16. The DNA sequence of claim 2 wherein said first and second peptide linkers are about 10 to about 50 amino acids in length.

17. The DNA sequence of claim 16 wherein said linkers are about 12 to about 30 amino acids in length.

18. The DNA sequence of claim 17 wherein said linkers are about 25 amino acids in length.

19. The DNA sequence of claim 18 wherein said linkers consist of the 25 amino acid sequence (SEQ ID NO: 5), Leu-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Leu.

20. The DNA sequence of claim 1 wherein the sequence coding for the first polypeptide comprises a base sequence whose expression product has the amino acid sequence (SEQ ID NO: 2) of Asp Ile Val Met Ser Gln Ser Pro Ser Ser Leu Pro Val Ser Val Gly Glu
Lys Val Thr Leu Ser Cys Lys Ser Ser Gln Ser Leu Leu Tyr Ser Gly Asn
Gln Lys Asn Tyr Leu Ala Trp Tyr Gln Gln Lys Pro Gly Gln Ser Pro
Lys Leu Leu Ile Tyr Trp Ala Ser Ala Arg Glu Ser Gly Val Pro Asp Arg
Phe Thr Gly Ser Gly Ser Gly Thr Asp Phe Thr Leu Ser Ile Ser Ser Val
Lys Thr Glu Asp Leu Ala Val Tyr Tyr Cys Gln Gln Tyr Tyr Ser Tyr
Pro Leu Thr Phe Gly Ala Gly Thr Lys Leu Val Leu Lys and the sequence coding for the second polypeptide comprises a base sequence whose expression product has the amino acid sequence (SEQ ID NO: 4) of Glu Val Gln Leu Gln Gln Ser Asp Ala Glu Leu Val Lys Pro Gly Ala
Ser Val Lys Ile Ser Cys Lys Ala Ser Gly Tyr Thr Phe Thr Asp His Ala
Ile His Trp Val Lys Gln Asn Pro Glu Gln Gly Leu Glu Trp Ile Gly Tyr
Phe Ser Pro Gly Asn Asp Asp Phe Lys Tyr Asn Glu Arg Phe Lys Gly
Lys Ala Thr Leu Thr Ala Asp Lys Ser Ser Ser Thr Ala Tyr Val Gln Leu
Asn Ser Leu Thr Ser Glu Asp Ser Ala Val Tyr Phe Cys Thr Arg Ser
Leu Asn Met Ala Tyr Trp Gly Gln Gly Thr Ser Val Thr Val Ser Ser.

21. The DNA sequence of claim 20 wherein the sequence coding for the first polypeptide comprises a base sequence (SEQ ID NO: 1) of GAC ATT GTG ATG TCA CAG TCT CCA TCC TCC CTA CCT
GTG TCA GTT GGC GAG AAG GTT ACT TTG AGC TGC AAG
TCC AGT CAG AGC CTT TTA TAT AGT GGT AAT CAA AAG
AAC TAC TTG GCC TGG TAC CAG CAG AAA CCA GGG CAG
TCT CCT AAA CTG CTG ATT TAC TGG GCA TCC GCT AGG
GAA TCT GGG GTC CCT GAT CGC TTC ACA GGC AGT GGA
TCT GGG ACA GAT TTC ACT CTC TCC ATC AGC AGT GTG
AAG ACT GAA GAC CTG GCA GTT TAT TAC TGT CAG CAG
TAT TAT AGC TAT CCC CTC ACG TTC GGT GCT GGG ACC
AAG CTG GTG CTG AAG and the sequence coding for the second polypeptide comprises a base sequence (SEQ ID NO: 3) of GAG GTT CAG TTG CAG CAG TCT GAC GCT GAG TTG GTG
AAA CCT GGG GCT TCA GTG AAG ATT TCC TGC AAG GCT
TCT GGC TAC ACC TTC ACT GAC CAT GCA ATT CAC TGG
GTG AAA CAG AAC CCT GAA CAG GGC CTG GAA TGG ATT
GGA TAT TTT TCT CCC GGA AAT GAT GAT TTT AAA TAC
AAT GAG AGG TTC AAG GGC AAG GCC ACA CTG ACT GCA
GAC AAA TCC TCC AGC ACT GCC TAC GTG CAG CTC AAC
AGC CTG ACA TCT GAG GAT TCT GCA GTG TAT TTC TGT
ACA AGA TCC CTG AAT ATG GCC TAC TGG GGT CAA GGA
ACC TCA GTC ACC GTC TCC TCA.

22. The DNA sequence of claim 1 wherein said first and second peptide linkers are about 10 to about 50 amino acids in length.

23. The DNA sequence of claim 22 wherein said linkers are about 25 amino acids in length.

* * * * *